United States Patent

Motoki et al.

[11] Patent Number: 6,036,636
[45] Date of Patent: Mar. 14, 2000

[54] ENDOSCOPE WITH TIP PORTION DISPOSED ON DISTAL SIDE OF INSERTION PORTION

[75] Inventors: Nobuyuki Motoki, Hino; Yutaka Konomura, Tachikawa, both of Japan

[73] Assignee: Olympus Optical Co., Ltd., Tokyo, Japan

[21] Appl. No.: 08/968,579

[22] Filed: Nov. 13, 1997

[30] Foreign Application Priority Data

Nov. 18, 1996 [JP] Japan .................................. 8-306711
Jun. 4, 1997 [JP] Japan .................................. 9-146853

[51] Int. Cl.[7] .................................................. A61B 1/008
[52] U.S. Cl. ........................ 600/146; 600/151; 600/141
[58] Field of Search .................................. 600/141, 143, 600/146, 151, 127, 136; 604/95, 280

[56] References Cited

U.S. PATENT DOCUMENTS

| | | | |
|---|---|---|---|
| 4,198,960 | 4/1980 | Utsugi ...................................... | 600/146 |
| 4,290,421 | 9/1981 | Siegmund ................................ | 600/146 |
| 4,790,624 | 12/1988 | Van Hoye et al. . | |
| 4,846,573 | 7/1989 | Taylor et al. ........................... | 600/143 |
| 5,251,611 | 10/1993 | Zehel et al. . | |
| 5,318,008 | 6/1994 | Bullard .................................... | 600/146 |
| 5,398,670 | 3/1995 | Ortiz et al. .............................. | 600/109 |
| 5,522,788 | 6/1996 | Kuzmak . | |

FOREIGN PATENT DOCUMENTS 9-297270 11/1997 Japan .

*Primary Examiner*—John P. Leubecker
*Attorney, Agent, or Firm*—Pillsbury Madison & Sutro LLP

[57] ABSTRACT

In an endoscope, an elastic member made of a super elastic alloy, for instance, bridges the distal end portion of an insertion portion and the proximal end portion of a tip portion so that a space portion having a given interval is formed in between. A curving mechanism advances or retreats a manipulation wire that extends from the tip portion to the proximal side of the insertion portion, whereby curving or bending occurs at the space portion between the tip portion and the insertion portion.

86 Claims, 23 Drawing Sheets

Fig. 14(a)
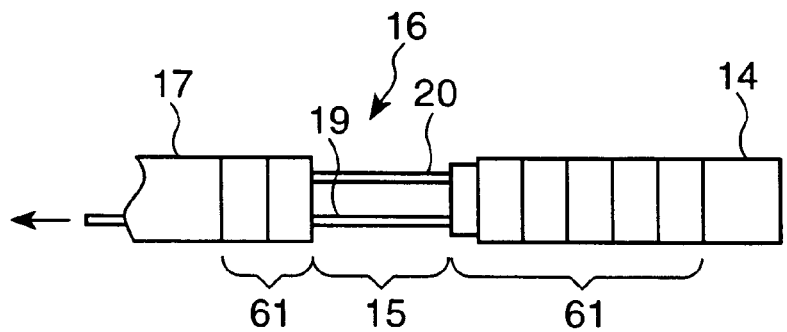
Fig. 14(b)
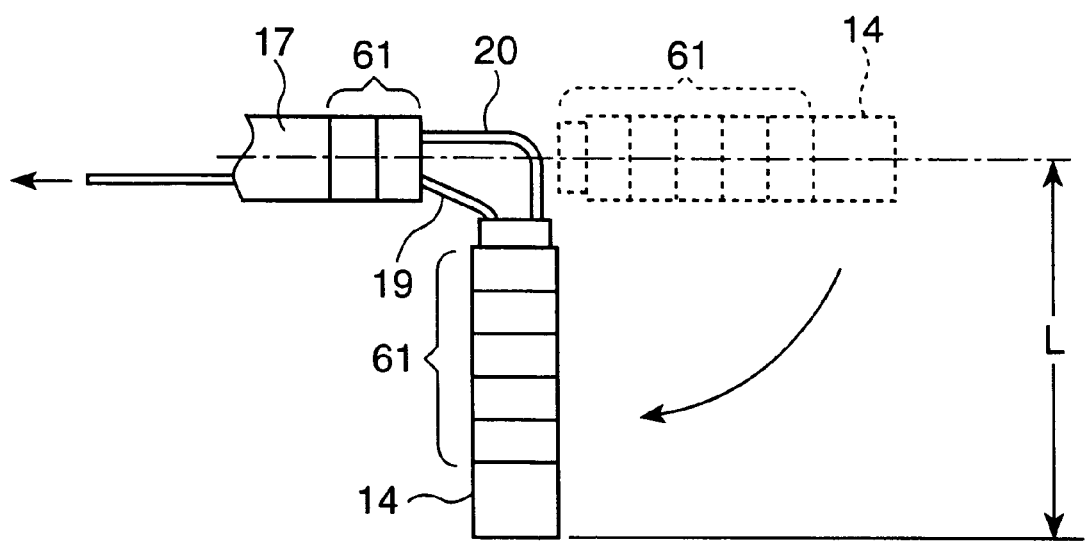

Fig. 15(a)
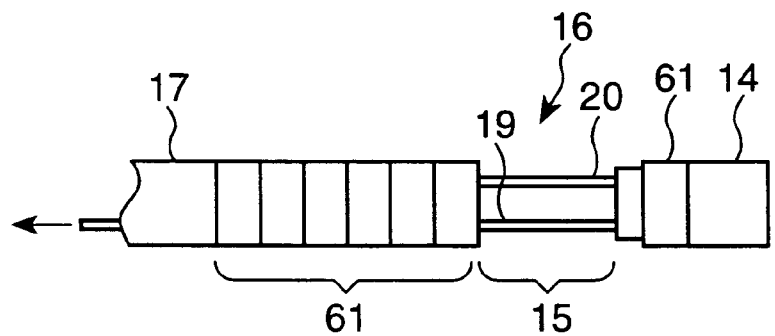
Fig. 15(b)
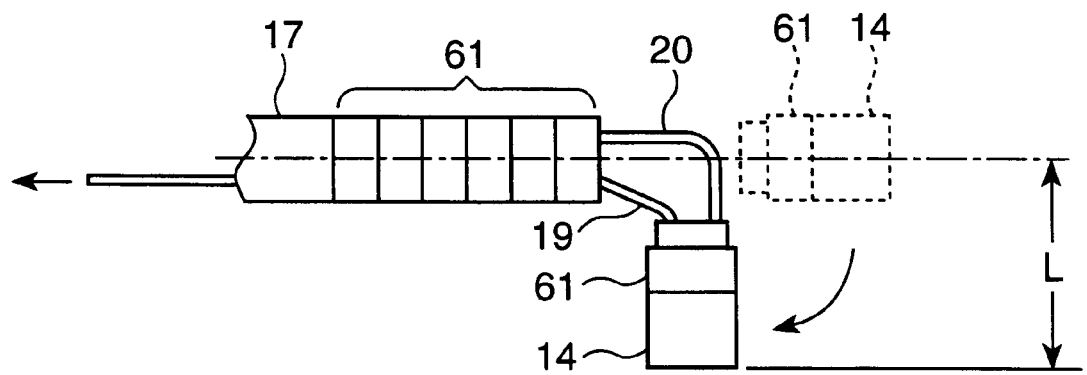

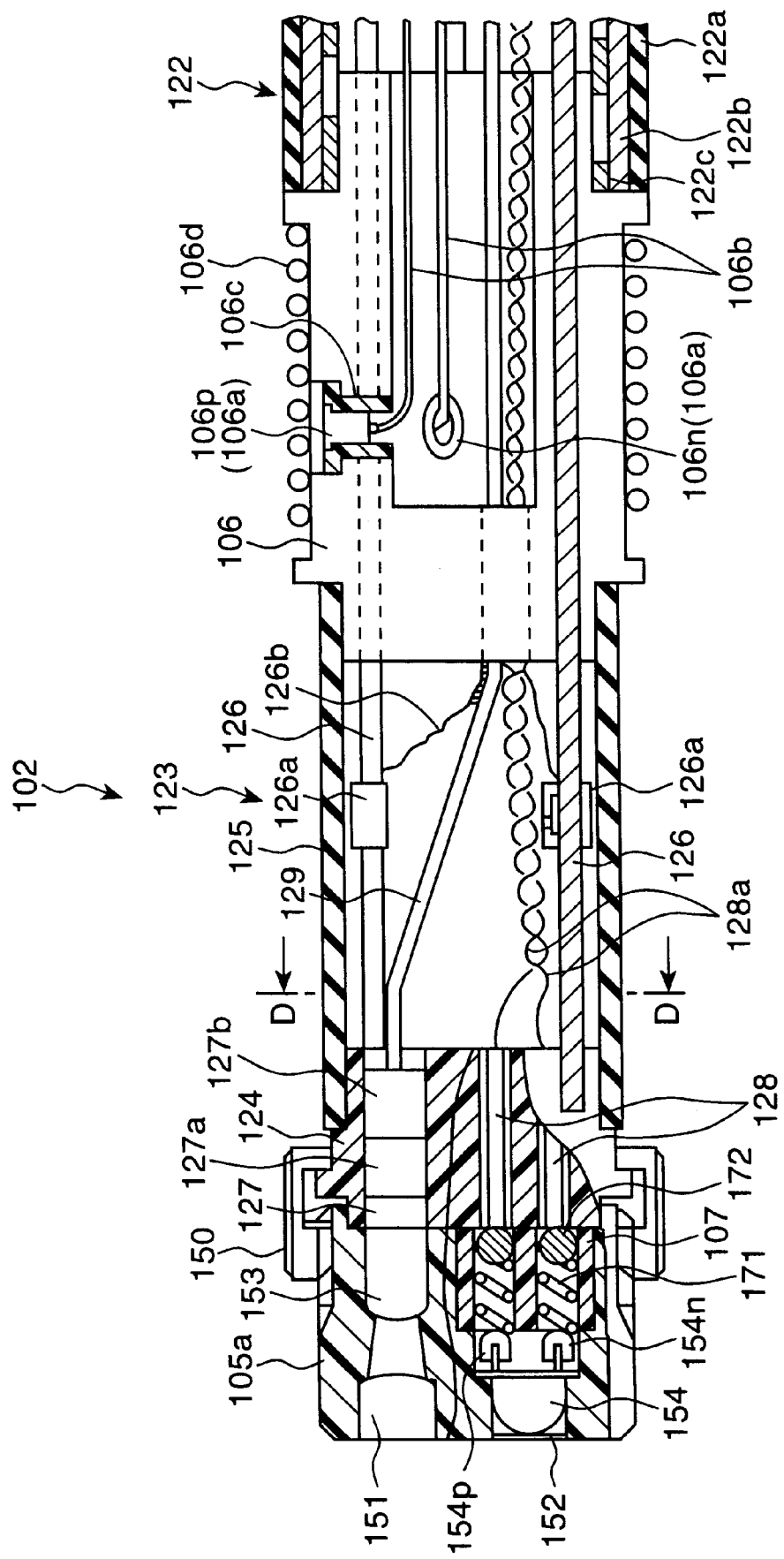

ENDOSCOPE WITH TIP PORTION DISPOSED ON DISTAL SIDE OF INSERTION PORTION

BACKGROUND OF THE INVENTION

1. Field of the invention

The present invention relates to an endoscope and, more specifically, to an endoscope featured by a curving mechanism for curving a curving portion.

2. Description of the Related Art

In a non-destructive inspection of compressor blades (hereinafter referred to as "blades") inside a jet engine by means of an industrial endoscope, there may be found damage such as a nick or a crack in a blade edge as caused by sucking of a bird, a stone, a piece of ice, or the like during operation of the jet engine.

In such a case, even if a damaged portion is small, if the jet engine is used without repairing it, stress may be concentrated on the damaged portion, possibly enlarging the damaged portion. When a damaged blade becomes not suitable for use, a common procedure is to disassemble and repair the jet engine. The damaged blade is removed from the engine, and is repaired by grinding into such a shape that there occurs no stress concentration on the damaged portion or replaced by a new one. However, the procedure of disassembling an engine and performing a grinding operation every time a small damaged portion is found has a problem that the repairing takes undue cost and time.

In general, a jet engine has, approximately for each blade, a hole (hereinafter referred to as "access port") for inspection of the blade. Various industrial endoscope apparatuses have been proposed that can repair, by grinding, a damaged portion of a blade edge to avoid stress concentration during operation without disassembling the engine such that a processing device mounted with a rotary processing member at its tip is inserted, together with an industrial endoscope, into the inside of the engine through the access port, then the rotary processing member located at the tip is opposed to the blade by bending the tip portion of the processing device, and finally the rotary processing member is rotated.

There is a certain distance between each access port and the corresponding blade, and the distance depends on the location in an engine and the type of engine. Further, after the processing device is inserted into the engine, the rotary processing member needs to be brought into contact with the blade by curving the tip portion of the endoscope apparatus.

Conventionally, as disclosed in, for instance, U.S. Pat. Nos. 5,251,611 and 5,522,788, the curving structure of ordinary endoscopes is used in which to obtain a curve a curving portion is formed by connecting together a plurality of block members. However, in this case, because of a gap between the opposed faces of the curving blocks of the curving portion, the portion on the tip side of the curving portion easily wobbles due to reaction force of grinding, disabling stable operation. Further, since the curving portion has a certain curvature, the accessibility is poor when a blade close to the access port is to be ground. U.S. Pat. No. 5,522,788 has an additional problem that the length of the portion on the tip side of the curving location cannot be changed freely as occasion demands.

U.S. Pat. No. 4,790,624 proposes a prior art technique having a curving structure that can be curved at a very small radius of curvature. This is configured such that a bending portion having a given space is formed between a tip member and an insertion member and a bending member consisting of a plurality of shape-memory alloy elements is provided in the bending portion. Bending is effected by controlling the heating of the shape-memory alloy elements of the bending member.

However, U.S. Pat. No. 4,790,624 has problems that to obtain a curve it is necessary to continue heating the shape-memory alloy elements, and that a fine temperature control for the curve control is difficult.

In view of the above, the present assignee filed Japanese Patent Application No. Hei. 8-109586. FIGS. 1 and 2 show this apparatus.

This apparatus comprises a processing device main body 301, a rotary processing member 302 and an endoscope 303. The processing main body 301 is composed of an insertion portion 304 and a tip member 302. A bending portion 306 is formed between the insertion portion 304 and the tip member 305 so as to provide a given space in between. As shown in FIG. 2, having a hinge structure, the bending portion 306 is bent by means of a manipulation wire 309 that is pulled as a rotation adjustment knob 308 is rotated. The processing device main body 301 guides the rotary processing member 302 and the endoscope 303 to the tip member 305. To accommodate the fact that the distance between an access port and a blade varies case by case, adaptors 310 having a plurality of lengths are provided for the tip member 305 to change the distance between the bending portion 306 and the rotary processing means 302.

However, since the bending portion 306 has the hinge structure, the above configuration has a problem that the bending portion 306 does not have a sufficient spatial margin for accommodation of such internal components as the rotary processing device 302 and the endoscope 303. To secure a sufficient spatial margin, the diameter of the insertion portion 304 including the bending portion 306 necessarily increases. On the other hand, to decrease the diameter, because of the insufficient spatial margin, it is necessary to thin a rotary shaft for rotating the rotary processing member 302 or an image guide and a light guide in the endoscope 303. If the image guide is thinned, there occurs a problem that an image having a sufficient number of pixels cannot be obtained. If the light guide is thinned, there arises a problem that illumination of sufficient brightness cannot be obtained. If the rotary shaft is thinned, there occurs a problem of insufficient strength.

The adaptors 310 are attached and removed to change the distance between the bending portion 306 and the rotary processing member 302. However, this is associated with problems that the operation of attachment and detachment of the adaptors 310 is complex and that the preparation of a plurality of replacement adaptors 310 having different lengths is costly.

SUMMARY OF THE INVENTION

The present invention has been made in the above circumstances, and an object of the invention is to provide an endoscope having a curving portion or a bending portion that secures sufficient space for internal components and can maintain a curve angle in a stable manner.

Specifically, an object of the invention is to provide an endoscope in which the portion on the tip side of the curving or bending portion does not wobble.

Another object of the invention is to provide an endoscope which allows the position of the curving or bending portion to be adjusted easily when occasion demands.

Another object of the invention is to provide an endoscope which secures a space for accommodating components incorporated in the curving or bending portion.

Another object of the invention is to provide an endoscope in which a manipulation relating to a curving or bending control can be made easily.

A further object of the invention is to provide an endoscope having a curving portion that can be curved to an arbitrary direction.

A still further object of the invention is to provide an endoscope having an eddy current examination probe for non-destructive inspection of damage in mechanical members.

The invention provides an endoscope comprising an elongate insertion portion; a tip portion disposed on a distal side of the insertion portion; an elastic member bridging a distal end portion of the insertion portion and a proximal end portion of the tip portion so as to form therebetween a space portion having a given interval; a manipulation wire disposed at a position deviated from a central axis of the space portion, and extending to a proximal side of the insertion portion past the space portion, one end of the manipulation wire being fixed to the tip portion; and a curving mechanism connected to a proximal end portion of the manipulation wire, for changing a direction of the tip portion at the space portion by advancing or retreating the manipulation wire.

In the endoscope of the invention, the space portion is formed by the elastic member between the distal end portion of the insertion portion and the proximal end portion of the tip portion, and the space portion can be curved or bent by advancing or retreating the manipulation wire by the curving mechanism. Therefore, the curving portion can be obtained which secure sufficient space for internal components and can maintain a curve angle in a stable manner.

BRIEF DESCRIPTION OF THE DRAWINGS

FIGS. 14(*a*)–14(*b*) and 15(*a*)–15(*b*) illustrate action of the curving portion that is attained by the blocks shown in FIG. 12;

FIG. 21 is a sectional view showing a tip-side structure of the insertion portion shown in FIG. 18;

DETAILED DESCRIPTION OF THE PREFERRED EMBODIMENTS

Embodiment 1

FIGS. 3–8 relate to a first embodiment of the present invention.

Figure 1:
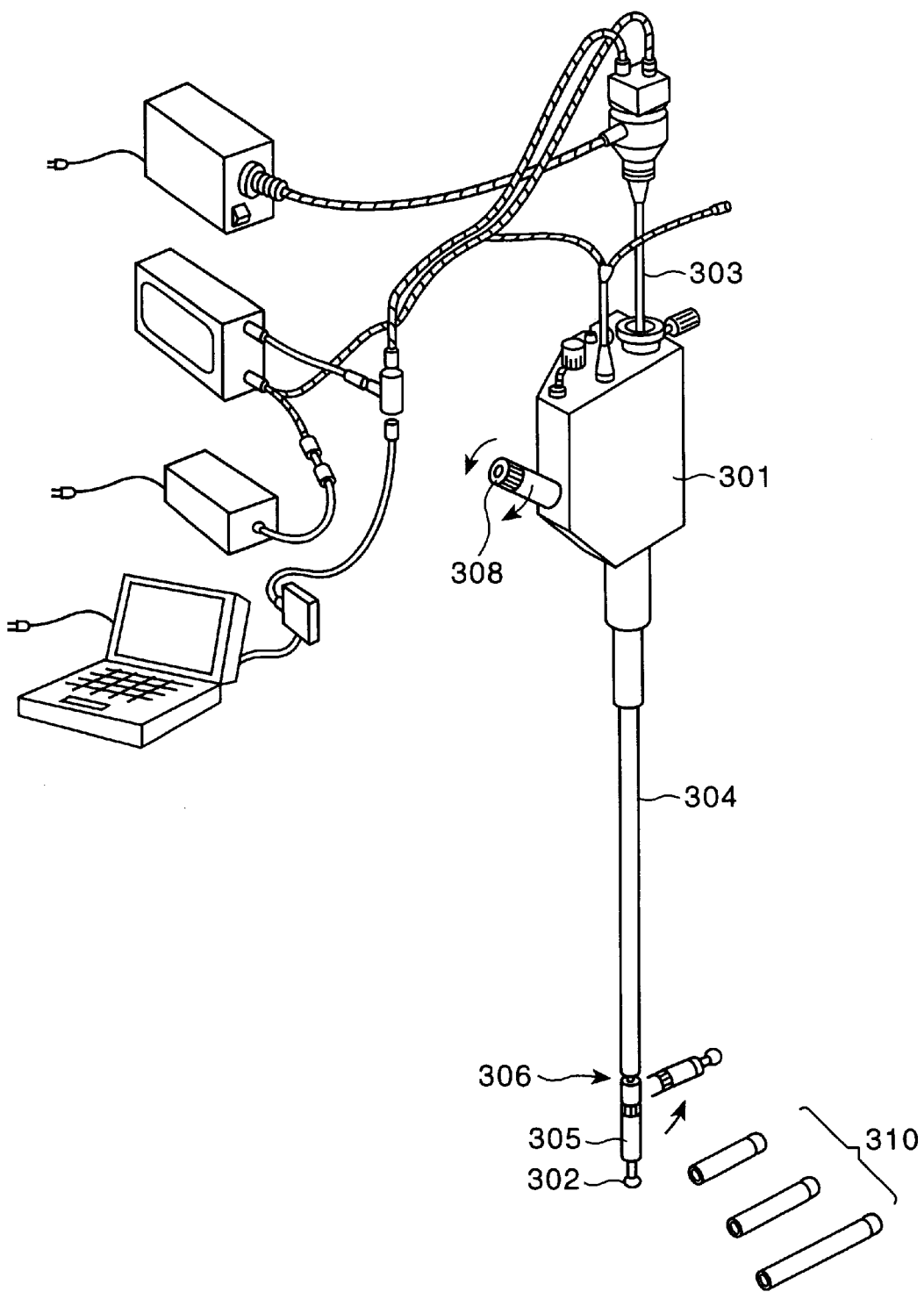
FIG. 1 shows the configuration of an industrial endoscope apparatus previously filed by the present assignee.
Figure 2:
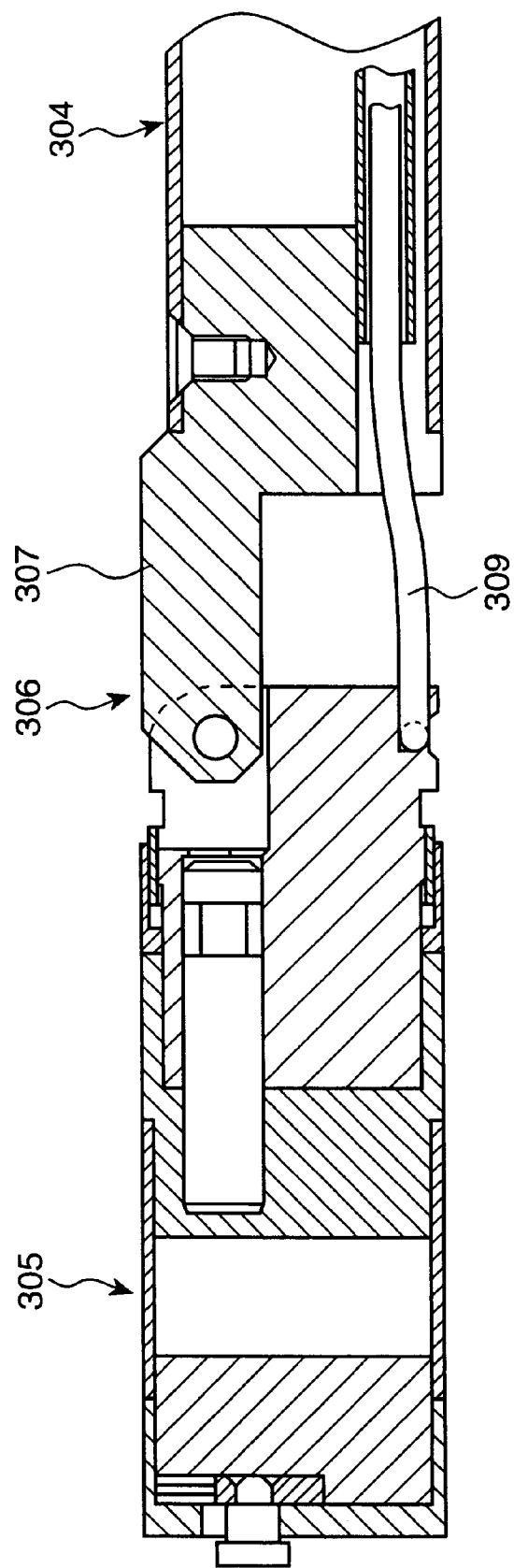
FIG. 2 is a sectional view showing a bending structure of a processing device main body shown in FIG. 1.
Figure 3:
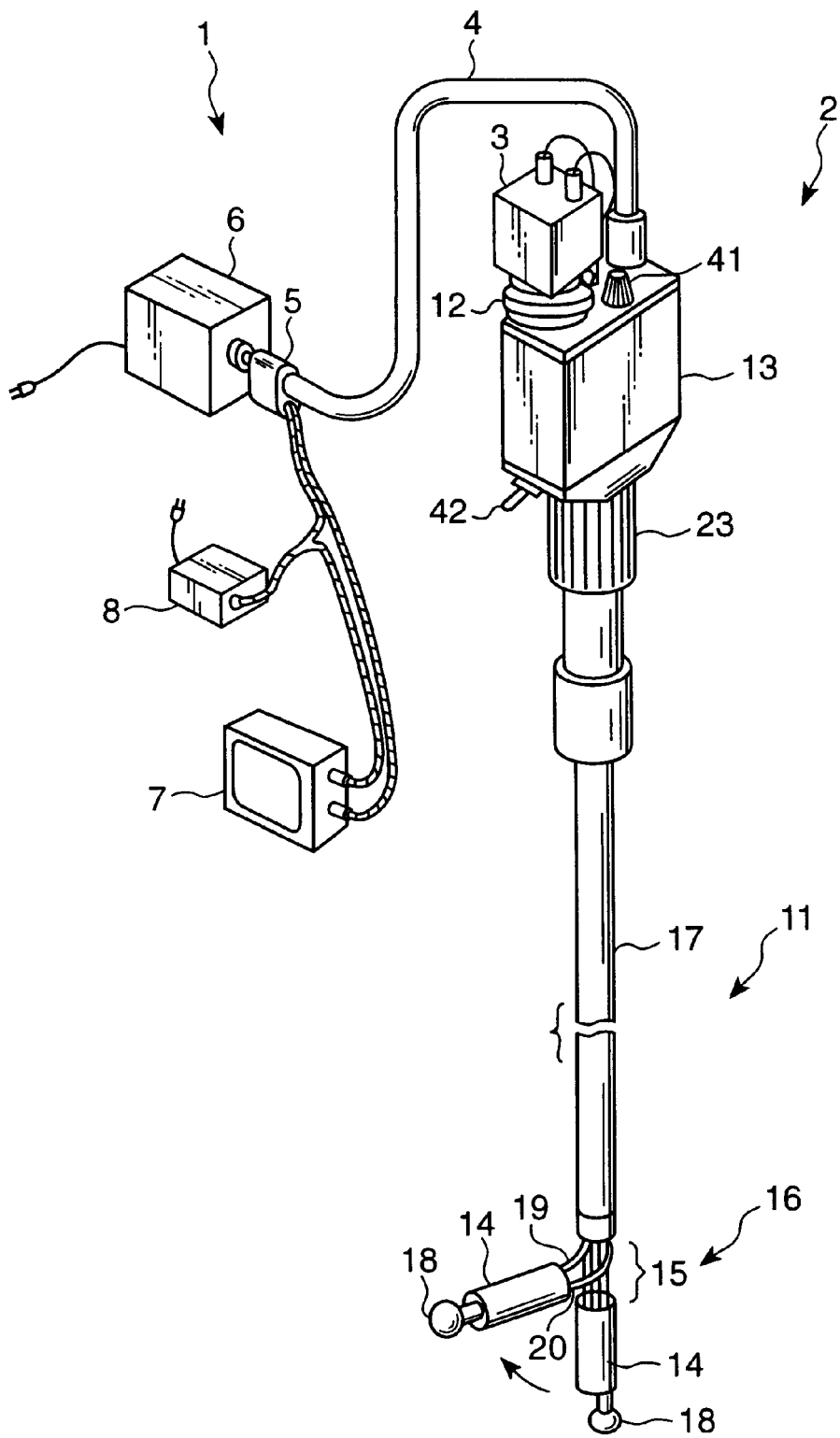
FIG. 3 shows the configuration of an industrial endoscope apparatus according to a first embodiment of the invention.

As shown in FIG. 3, an industrial endoscope processing apparatus 1 according to the first embodiment consists of the following components. When inserted in the inside of a jet engine, for instance, an industrial endoscope 2 enables observation of a body to be ground and grinds it. A CCD camera 3 is threadedly connected to a proximal end portion of the industrial endoscope 2. A light source device 6 is connected to a light source connector 5 that is provided at the tip of an universal cable 4 extending from a proximal end portion of the industrial endoscope 2. A LCD monitor 7 for displaying an image of a body to be ground is electrically connected to the CCD camera 3 via the universal cable 4. A power supply 8 is electrically connected to the industrial endoscope 2, the CCD camera 3, and the LCD monitor 7 and supplies power to those devices.

The industrial endoscope 2 comprises an elongate insertion portion 11 and a box-shaped manipulation portion 13 having a mount portion 12 and provided on the proximal end side of the insertion portion 11. The universal cable 4 extends from the mount portion 12, and the CCD camera 3 is detachably connected to the mount portion 12. The insertion portion 11 includes, in order from the tip, a tip portion 14, a curving portion 16 having a plurality of wire members (described later) and a predetermined interval 15, and a rigid, an elongate insertion tube 17. A grindstone 18 that is provided at a rotational force transmission member (described later) and serves to grind a subject body projects from the tip portion 14.

The plurality of wire members of the curving portion 16 consist of two first wire members 19 and two second wire members 20. The first and second wire members 19 and 20 are metal wire members that are high in both straight extendability and flexibility, such as made of a super elastic alloy that is a Ni—Ti alloy.

Although in this embodiment the first wire members 19 and the second wire members 20 are each a set of two wire members, they may each be a single wire rod or a set of three or more wire members.

As described later, the first wire members 19 and the second wire members 20 are provided so as to be located at inside and outside positions, respectively, when the curving portion 16 is curved.

Figure 4:
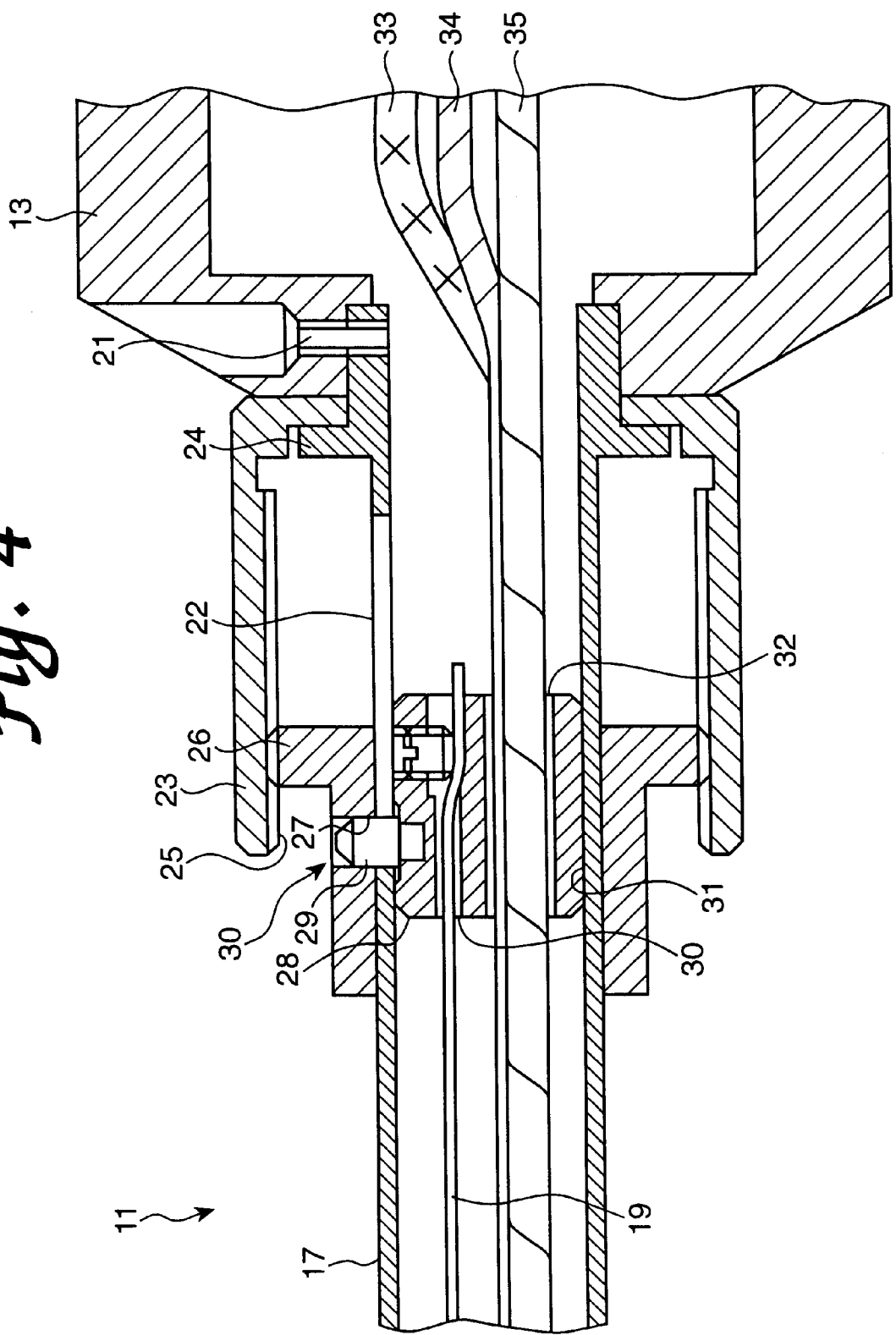
FIG. 4 is a sectional view showing a structure of a tip-side portion of a manipulation portion and a proximal end portion of an insertion tube that are shown in FIG. 3.

As shown in FIG. 4, the tip side of the manipulation portion 13 and the proximal end side of the insertion tube 17 are fixed to each other with a fixing screw 21. The proximal end side of the insertion tube 17 is formed with a long groove 22. A ring-shaped adjustment ring 23 (see FIG. 3) is interposed between the manipulation portion 13 and a flange portion 24 of the insertion tube 17 so as to be rotatable in the circumferential direction.

A slide cylinder 26 is threadedly engaged with inside female threads 25 of the adjustment ring 23. The slide cylinder 26 is slidably attached to the outer circumferential surface of the insertion tube 17, and is formed with a slide pin hole 27.

A slide member 28 is slidably fitted in the inside surface of the insertion tube 17. A slide pin 29 is fixed to the slide member 28. The slide pin 29 is also fixed to the slide pin hole 27 past the long groove 22. Thus, the slide pin 29 connects the slide cylinder 26 and the slide member 28.

The slide member 28 is formed with a stepped fixing hole 30, in which the first wire members 19 are inserted. The first wire members 19 are fixed to the slide member 28 with a fixing vis 31 in the lateral direction. Thus, the first wire members 19 can be moved (advanced/retreated) in the longitudinal direction by rotating the adjustment ring 23.

On the other hand, the slide member 28 is formed with an insertion hole 32, which allows insertion, with a gap, of internal components such as a light guide fiber bundle (hereinafter referred to as "light guide") 33 for transmitting illumination light from the light source device 6 to the tip portion 14, an image guide fiber bundle (hereinafter referred to as "image guide") 34 for transmitting an image of a body to be ground to the mount portion 12 that is connected to the CCD camera 3, and a flexible, rotational force transmission member 35 for rotating the grindstone 18.

Although not shown any drawings, the mount portion 12 is provided with an imaging optical system for forming an image that is transmitted by the image guide 34 on the imaging surface of the CCD camera 3. Although not shown in any drawings, a motor and a motor control circuit for controlling the rotation of the motor are provided inside the manipulation portion 13. The rotational force transmission member 35 is connected to the rotary shaft of the motor.

Figure 5:
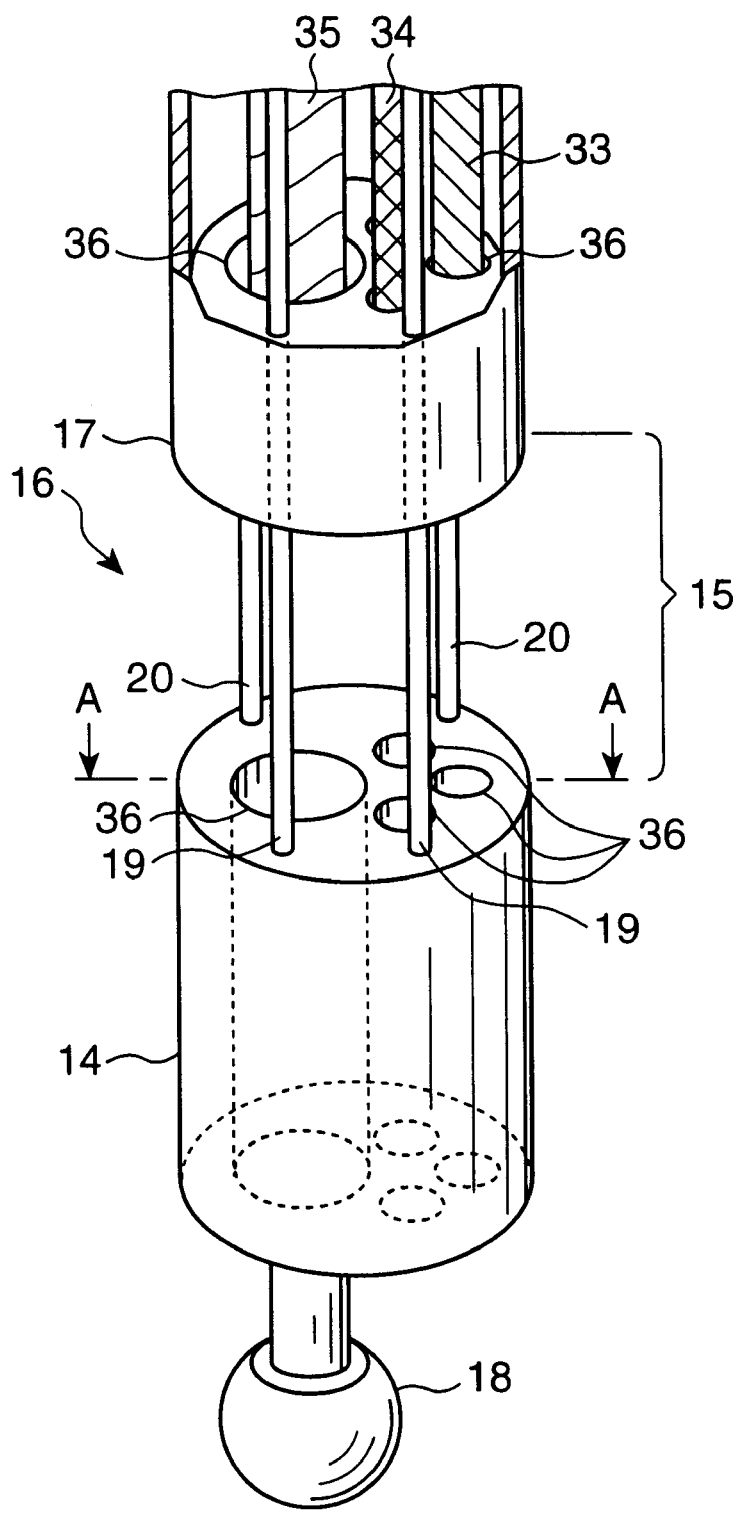
FIG. 5 shows a structure of a tip portion and a curving portion that are shown in FIG. 3.
Figure 6:
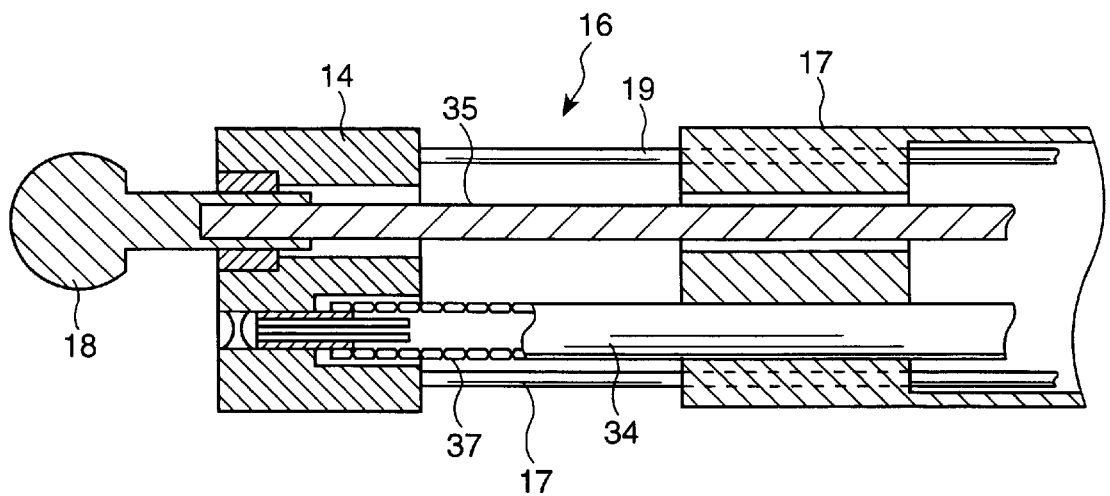
FIG. 6 is a sectional view taken along line A—A in FIG. 5.

As shown in FIG. 5, each of the insertion tube 17 and the tip portion 14 is formed with a plurality of insertion holes 36 that allow insertion of the internal components. That is, through the insertion holes 36, the light guide 33, the image guide 34, and the rotational force transmission member 35 are inserted, with gaps, into the insertion tube 17, the curving portion 16, and the tip portion 14. As shown in FIG. 6, the image guide 34 and the light guide 33 (not shown in FIG. 6) are fixed to the tip of the tip portion 14 and the rotational force transmission member 35 having the grindstone 18 at its tip is fixed to the tip of the tip portion 14 such that the grindstone 18 projects from the tip of the tip portion 14. The first wire members 19 also pass through the insertion holes 36 of the insertion tube 17 and are fixed to the proximal end of the tip portion 14.

The image guide 34 is configured such that a bundle of optical fibers are covered with a Teflon tube 37. Although not shown in any drawings, the light guide 33 is similarly configured such that a bundle of optical fibers are covered with a Teflon tube. The covering with the Teflon tube 37 prevents deterioration of the bundle of optical fibers.

In FIG. 5, the light guide 33, the image guide 34, and the rotational force transmission member 35 are not shown in the curving portion 16 and the tip portion 14.

Returning to FIG. 3, a rotation adjustment knob 41 is provided on the rear end face of the manipulation portion 13. Electrically connected to the motor control circuit (not shown), the rotation adjustment knob 41 serves to control the rotation speed of the motor. A switch 42, which is provided on the front end face of the manipulation portion 13, serves to on/off-control the rotation of the motor via the motor control circuit (not shown).

Figure 7:
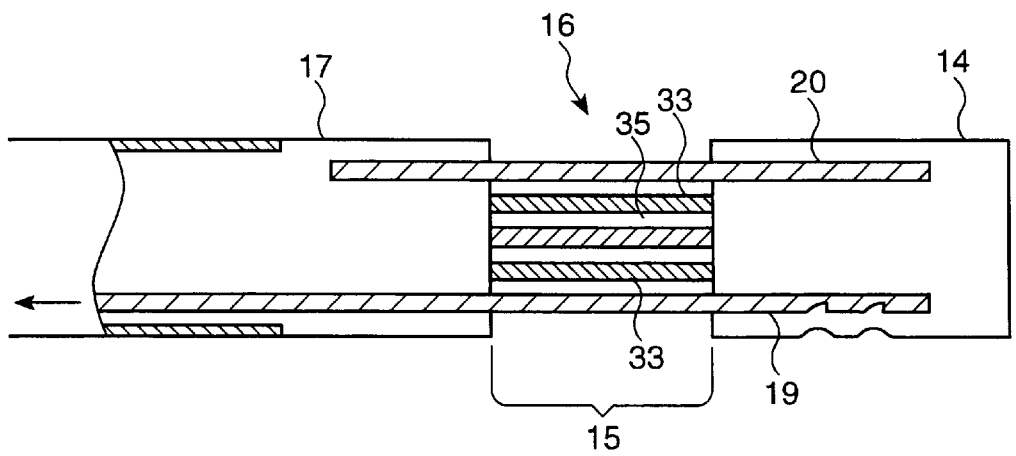
FIG. 7 illustrates how first and second wire members are fixed in the curving portion shown in FIG. 3.

As described above, the proximal ends of the first wire members 19 are fixed to the slide member 28 which moves in the axial direction as the adjustment ring 23 is rotated in the circumferential direction. As shown in FIG. 7, the tips of the first wire members 19 are fixed to the tip portion 14 by caulking. Thus, the first wire members 19 are mounted so as to be movable with respect to the insertion tube 17.

The second wire members 20 are fixed to the proximal end portion of the tip portion 14 and the tip portion of the insertion portion 11. The second wire members 20 determine the length of a gap 15, i.e., a given interval between the tip portion 14 and the insertion section 11. Thus, the curving portion 16 is constituted of the gap 15, the first wire members 19, and the second wire members 20. That is, the second wire members 20 bridge the tip portion 14 and the insertion portion 11 with a given space formed in between.

The second wire members 20 need not always be fixed; it suffices that the gap 15 of the curving portion 16 be formed in an uncurved state. For example, the second wire members 20 may be inserted in pouch-like holes (blind holes) that are provided in the tip portion 14 and the tip portion of the insertion tube 17 and are so deep in the longitudinal direction that the second wire members 20 do not drop even in a maximum curved state.

Next, the operation of the above-configured first embodiment will be described.

Upon connection of the power supply 8 and the light source device 6 to a socket, electricity is supplied from the power supply 8 to the LCD monitor 7, the industrial endoscope 2, and the CCD camera 3.

In the industrial endoscope 2, illumination light is supplied from the light source device 6 to the light guide 33 having an incident end face in the light source connector 5, transmitted to the tip portion 14 by the light guide 33 which is inserted in the universal cable 4 and the insertion portion 11, and finally emitted forward from the tip portion 14. An image of an inside portion of an engine being illuminated with the illumination light is transmitted by the image guide 34 to the mount portion 12 to which the CCD camera 3 is connected. Thus, the image is picked up by the CCD camera 3. A video signal is sent from the CCD camera 3 to the LCD monitor 7, whereby the image of the inside portion of the engine is checked and observed on the LCD monitor 7.

While the image of the inside portion of the engine is observed on the LCD monitor 7, the insertion portion 11 is inserted and the curving portion 16 is curved by rotating the adjustment ring 23 so that the grindstone 18 is opposed to a part to be ground of a subject body.

Then, the switch 42 is turned on to rotate the motor in the manipulation portion 13, to thereby rotate the grindstone 18 via the rotational force transmission member 35 which is connected to the rotary shaft of the motor. Thus, the part to be ground of the subject body is ground by the grindstone 18. At this time, the rotation speed of the motor can be changed by rotating the rotation adjustment knob 41. If the switch 42 is turned off, the rotation of the motor is stopped and the rotation of the grindstone 18 is also stopped.

The curving operation of the curving portion 16 will be described below with reference to FIGS. 8(a) and 8(b).

Figure 8A:
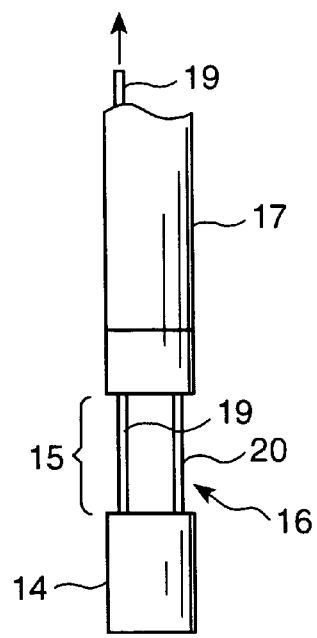
FIGS. 8(*a*) and 8(*b*) illustrate action of the curving portion that is caused by the first and second wire members shown in FIG. 3.

For example, if the adjustment ring 23 is rotated, for instance, clockwise in a state that the curving portion 16 is not curved (see FIG. 8(a)), the slide member 28 is pulled up toward the proximal side and the first wire members 19 are also pulled up toward the proximal side following the slide member 28. At this time, since the positions of both ends of the second wire members 20 do not vary, the second wire members 20 are just bent. Thus, as shown in FIG. 8(b), a desired curve is obtained in the curving portion 16.

Figure 8B:
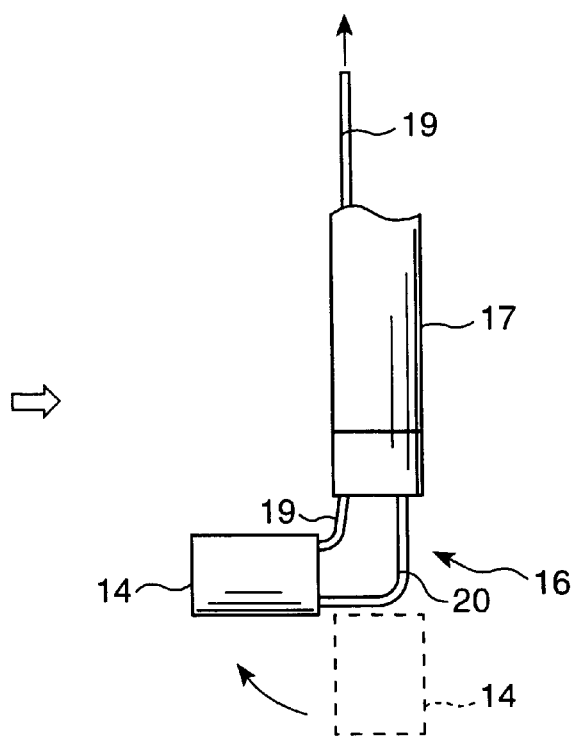

Since the first wire members 19 and the second wire members 20 in the first embodiment are made of a super elastic alloy that is high in both flexibility and straight extendability, the curving portion 16 is curved so as to assume approximately an L shape, i.e., a steep shape close to a right angle, or to assume a bent shape (see FIG. 8(b))

By changing the amount of rotation of the adjustment ring 23, the pulling force on the first wire members 19 is changed whereby the curve angle of the curving portion 16 can be adjusted to an arbitrary angle. Because of the use of the metal wire members, sufficient rigidity (sufficient strength for maintaining a curved shape) that is higher than in the case of using a coil, rubber, resin, or the like.

To recover the curving portion 16 now being curved to the original state, the adjustment ring 23 is rotated in the opposite direction. In response, the slide member 28 moves toward the tip and the first wire members 19 also move toward the tip following the slide member 28. As a result, the first wire members 19 that were pulled up toward the proximal side move to toward the tip, to cancel the curve of the curving portion 16. Since the first wire members 19 themselves are high in both flexibility and straight extendability, the insertion tube 17, the curving portion 16, and the tip portion 14 return to a straight state due to restitutive force of the first wire members 19 themselves.

As described above, the first embodiment provides an industrial endoscope that is featured as follows. Even with a simple structure in which the first wire members 19 made of a super elastic alloy are moved by the adjustment ring 23, the curving portion 16 can be curved at a small radius of curvature and a curve angle can be maintained stably. Further, since the curving mechanism consists of only the first wire members 19 and the second wire members 20, the curving portion 16 can secure sufficient space for the internal components.

Although in the first embodiment the curving portion 16 is curved by pulling the first wire members 19, it may be curved in the opposite manner, that is, by pushing the first wire members 19. That is, if the adjustment ring 23 is rotated, for instance, counterclockwise in a state that the curving portion 16 is not curved, the slide member 28 moves toward the tip and the first wire members 19 are pushed toward the tip following the slide member 28. At this time, since the positions of both ends of the second wire members 20 do not vary, the second wire members 20 are just bent. Thus, a desired curve is obtained in the curving portion 16.

The material of the first wire members 19 and the second wire members 20 is not limited to the super elastic alloy. For example, an elastic member made of a material that is high in both flexibility and straight extendability may be used. If a material that is low in flexibility were used, a sufficiently small radius of curvature would not be obtained and a sufficient curve would not be obtained due to high rigidity against curving. If a material that is low in straight extendability, the curving portion 16 would not return to a straight shape when a curve is canceled.

Although in the industrial endoscope 2 the light guide 33, the image guide 34, and the rotational force transmission member 35 are integrated, an endoscope having a soft insertion portion as disclosed in Japanese Patent Application No. Hei. 8-109586 of the present assignee may be inserted in a detachable manner.

Embodiment 2

FIGS. 9–17 relate to a second embodiment of the invention. The parts in the second embodiment that are the same as in the first embodiment are given the same reference numeral and detailed description therefor will be omitted.

Figure 9:
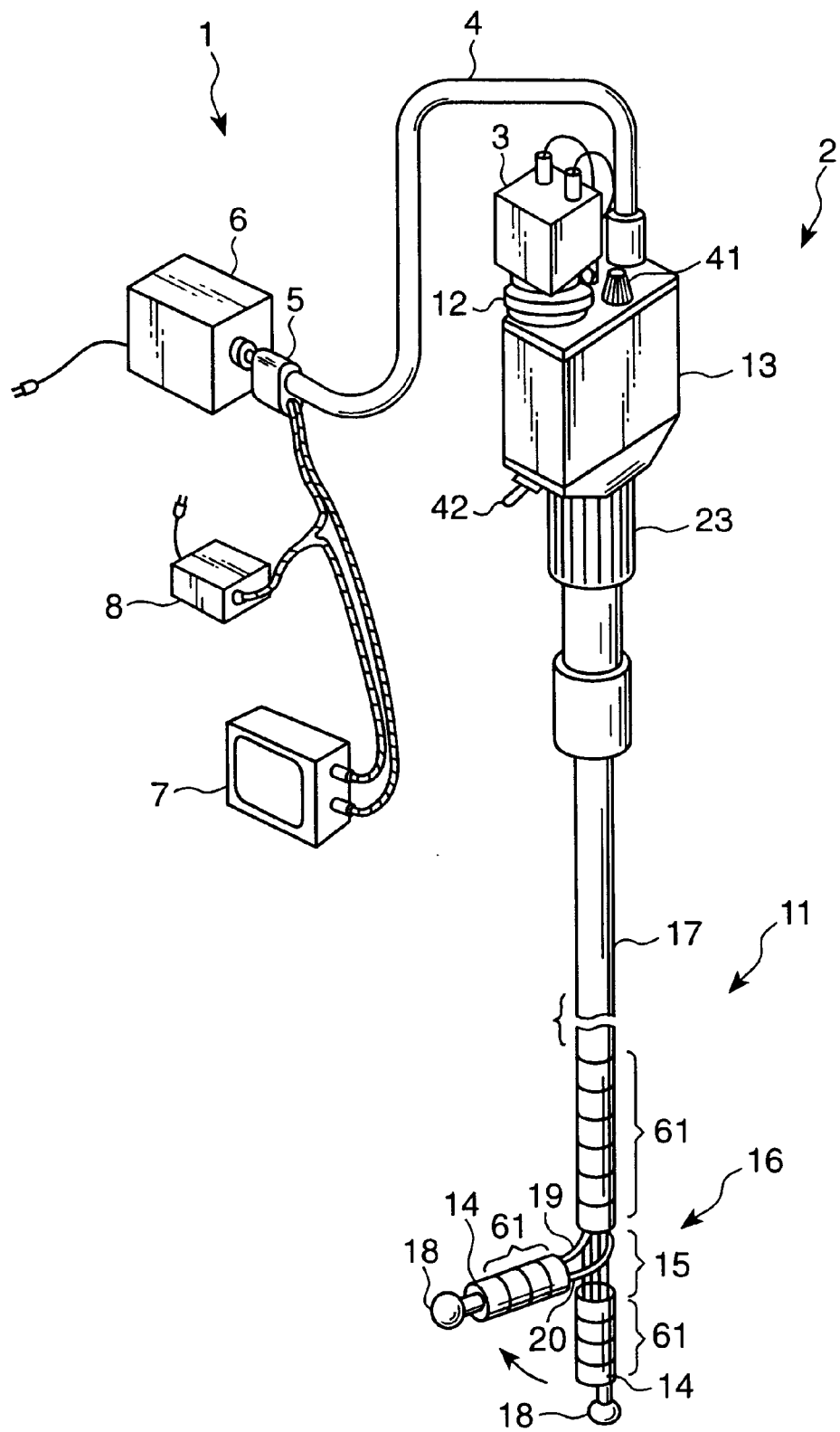
FIG. 9 shows the configuration of an industrial endoscope processing apparatus according to a second embodiment of the invention.

As shown in FIG. 9, an insertion portion 11 of an industrial endoscope 2 of the second embodiment consists of an insertion tube 17, a plurality of blocks 61 as tip portion length adjustment member that are arranged at the tip of the insertion tube 17 contiguously in the longitudinal direction, and a tip portion 14.

Figure 10:
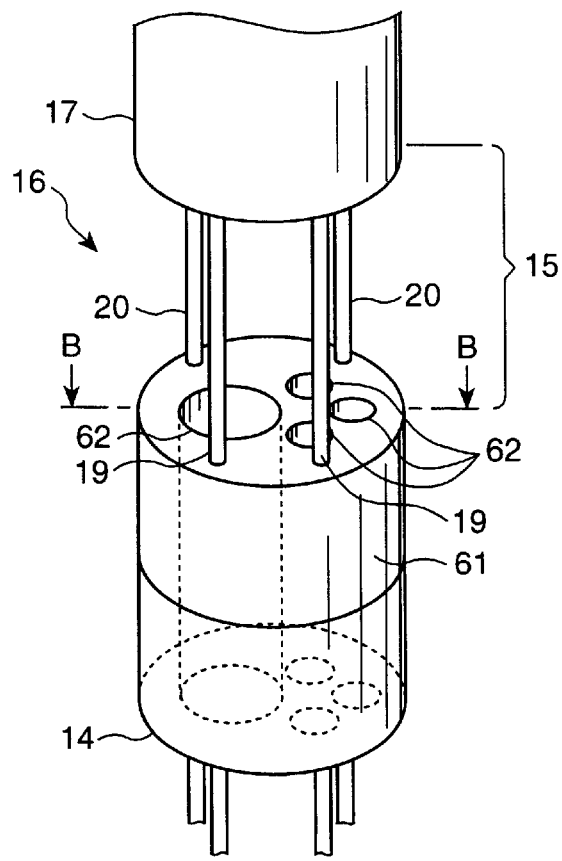
FIG. 10 shows a structure of a tip portion and a curving portion shown in FIG. 9.

As shown in FIG. 10, each of the contiguous blocks 61 is formed with insertion holes for insertion of internal components. The internal components, i.e., the light guide 33, the image guide 34, the rotational force transmission member 35, the first wire members 19, and the second wire members 20 are inserted, with gaps, in the insertion holes 62.

Figure 11:
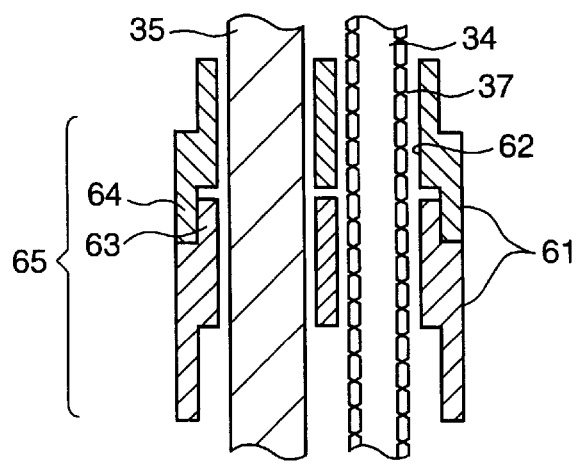
FIG. 11 is a sectional view taken along line B—B in FIG. 10.

As shown in FIG. 11, as in the case of the first embodiment, the image guide 34 is covered with a Teflon tube 37. Although not shown in FIG. 11, the light guide 33 is also covered with a Teflon tube in a similar manner. There are gaps between the insertion holes 62 and the internal components. Since the Teflon tube 37 has good slip performance, the internal component does not make a strong contact with the blocks 61 when the blocks 61 are moved. Therefore, it is possible to move the blocks 61 freely without paying any consideration to the friction with the internal component.

Each block 61 has a recess 63 and a protrusion 64 that constitute a fitting portion 65. The blocks 61 are connected together such that fitting is effected in the respective fitting portions 65. The fitting portions 65 are separably configured. The tip portion 14 is fitted in the tip of the front block 61 detachably and contiguously.

The second wire members 20 secure the interval between the insertion tube 17 and the tip portion 14 so that a gap 15 is formed in between even in a state that all of the plurality of blocks are connected to together. Since the respective blocks 61 are movable in the longitudinal direction, the gap 15 formed between the blocks 61 is also movable. The gap 15 and the exposed first and second wire members 19 and 20 constitute the curving portion 16. Thus, the curving portion 16 is rendered movable.

Figure 12:
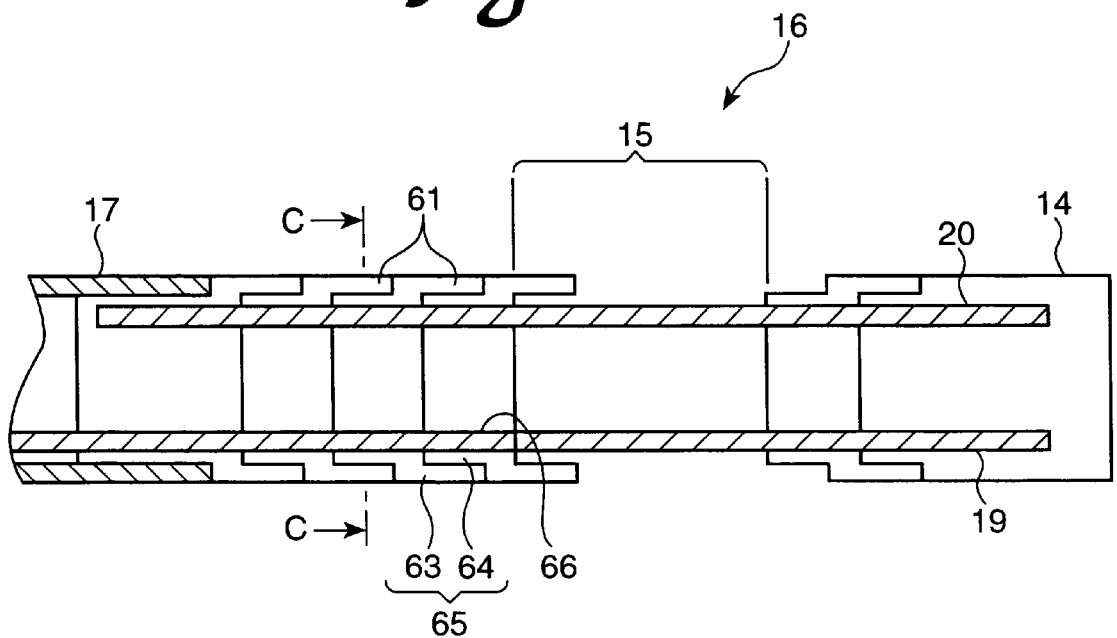
FIG. 12 illustrates the shape of blocks that constitute the curving portion shown in FIG. 9.

As shown in FIG. 12, adjacent ones of the blocks 61 are connected to each other by fitting the protrusion 64 into the recess 63. Fitting holes 66 for insertion of the first and second wire members 19 and 20 penetrate through each block 61 in the axial direction. As for the distance between the tip portion 14 and the tip of the insertion tube 17, the second wire members 20 secure the gap 15 so that it has a constant interval. The gap 15 can be located at an arbitrary position by moving part of the plurality of blocks 61.

Figure 13:
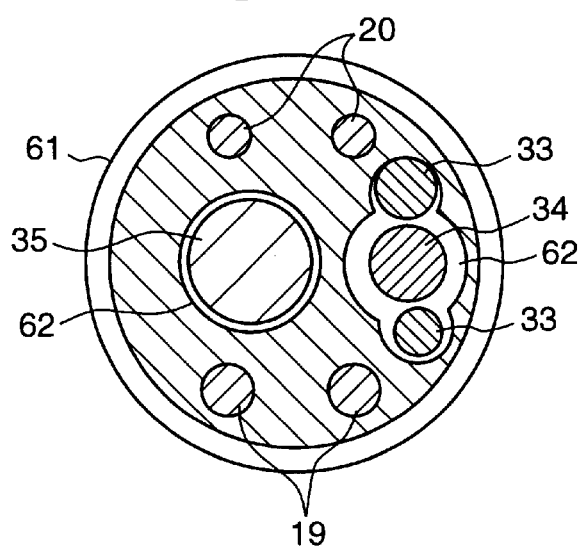
FIG. 13 is a sectional view taken along line C—C in FIG. 12.
Figure 16:
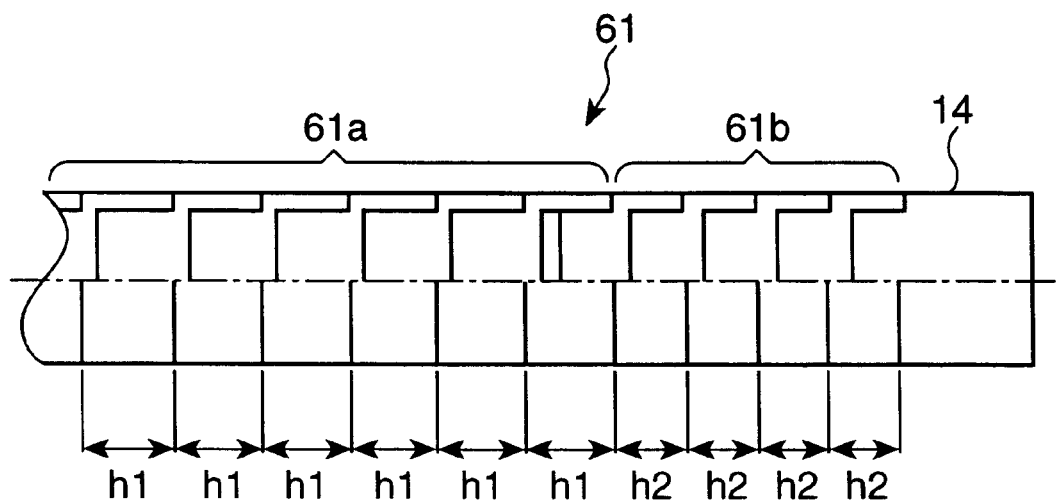
FIG. 16 shows a modification of the second embodiment and illustrates shapes of blocks that are modified from the blocks shown in FIG. 12.

As shown in FIG. 13, in each block 61, the light guide 33 and the image guide 34 are inserted, with gaps, in the insertion holes 62 that penetrate the block 61 in the axial direction. Similarly, the rotational force transmission member 35 is inserted, with a gap, in the insertion hole 62 that penetrates the block 61 in the axial direction.

The other structures are the same as in the first embodiment.

Next, the operation of the above-configured second embodiment will be described.

As shown in FIGS. 14(*a*), the gap 15 is formed at a first position by moving part of the blocks 61 in accordance with a known distance between an access port and a blade. Then, the tip portion 14, the insertion portion 11 is inserted into the access port with the tip portion 14 as the head. As in the case of the first embodiment, while an image is observed, a curving manipulation is performed as shown in FIG. 14(*b*) so that the grindstone 18 is opposed to a part to be ground of the blade, and then actual processing is performed.

Then, for the next processing, for instance, the gap 15 is formed at a second position by moving part of the blocks 61 in accordance with a known distance between another access port and a blade, as shown in FIG. 15(*a*). Thereafter, the curving portion 16 is curved by moving the first wire members 19 as shown in FIG. 15(*b*) and then actual processing is performed.

That is, grinding is performed after a length L between the curving portion 15 to the tip is changed by moving the curving portion 16 (gap 15) to the tip side as shown in FIGS. 14(*a*)–14(*b*) and 15(*a*)–15(*b*).

The remaining operation is the same as in the first embodiment.

As described above, in the second embodiment, the curving position can be formed at a desired position by changing the positions of part of the movable blocks 61; the curve position can be set easily only by moving part of the blocks 61.

Thus, the second embodiment provides the following advantages in addition to the advantages of the first embodiment:

(1) The length of the portion on the tip side of the curving portion 16 can easily be changed without adding any new members for setting the curve position.

(2) The length of the portion on the tip side of the curving portion 16 can easily be changed by a simple operation.

(3) The curving portion 16 can be constructed at a low cost even if the length of the portion on the tip side of the curving portion 16 needs to be variable.

In the second embodiment, the blocks 61 are connected to each other such that the protrusion 64 of each block 61 fits in the recess 63 of the adjacent block 61. A modification is possible in which among the blocks 61 blocks 61*a* on the side of the insertion tube 17 and blocks 61*b* on the side of tip portion 14 have different axial lengths h1 and h2 (h1>h2), respectively, and the curving portion 16 is formed from the block 61*b* where the axial length changes from h1 to h2.

In this case, the axial lengths of the recess 63 and the protrusion 64 of the fitting portion of the block 61 vary with the axial length of the block 61. The fitting gap of the protrusion 64 of the block 61*b* having the axial length h1 is shorter than that of the block 61*a* having the axial length h2, and hence the block 61*b* can be inserted and removed more easily.

The block(s) 61 may be either at least one block or a plurality of blocks that are connected to the proximal end portion of the tip portion 14 or the tip of the insertion tube 17. Further, the blocks 61 having different axial length may be a plurality of blocks that are arranged regularly or irregularly.

In this modification of the second embodiment, when a curve is formed in the same manner as in the first embodiment, the tip portion 14 receives force that pulls it toward the proximal side.

Figure 17:
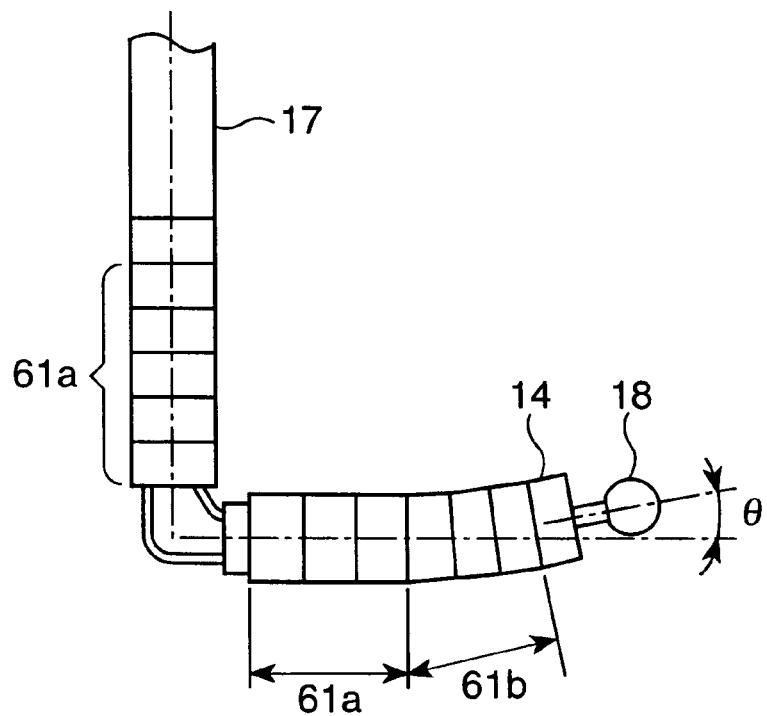
FIG. 17 illustrates action of the curving portion that is attained by the blocks shown in FIG. 16.

As shown in FIG. 17, the force of pulling the tip portion 14 causes the blocks 61 to deviate by slight fitting gaps at the fitting portions. Since a plurality of blocks 61 are connected together, deviations at a plurality of positions are accumulated whereby the portion on the tip side of the curving portion 16 is warped. Although a warp occurs in both of the range where the axial length is h1 and the range where the axial length is h2, the warp in the latter range is larger than the warp in the former range because of the shorter fitting length. The sum of both warp angles amounts to an angle θ that is added to the original curve angle.

Since the warps causes an angle that is larger than the curve angle that is originally given to the curving portion 16, the access range is increased as much. Further, since the original curve angle can be decreased, the load that is imposed by the curving on each internal component inserted in the curving portion 16 can be reduced.

In a case where the portion on the tip side of the curving portion needs to be short to perform a repair by grinding in the inside of a jet engine, a turbine blade cannot be accessed in a favorable state unless fine length adjustments are possible. The use of the shorter blocks 61*b* on the tip side is convenient in this point because they enable fine length adjustments.

Embodiment 3

FIGS. 18–28 relate to a third embodiment of the invention.

Figure 18:
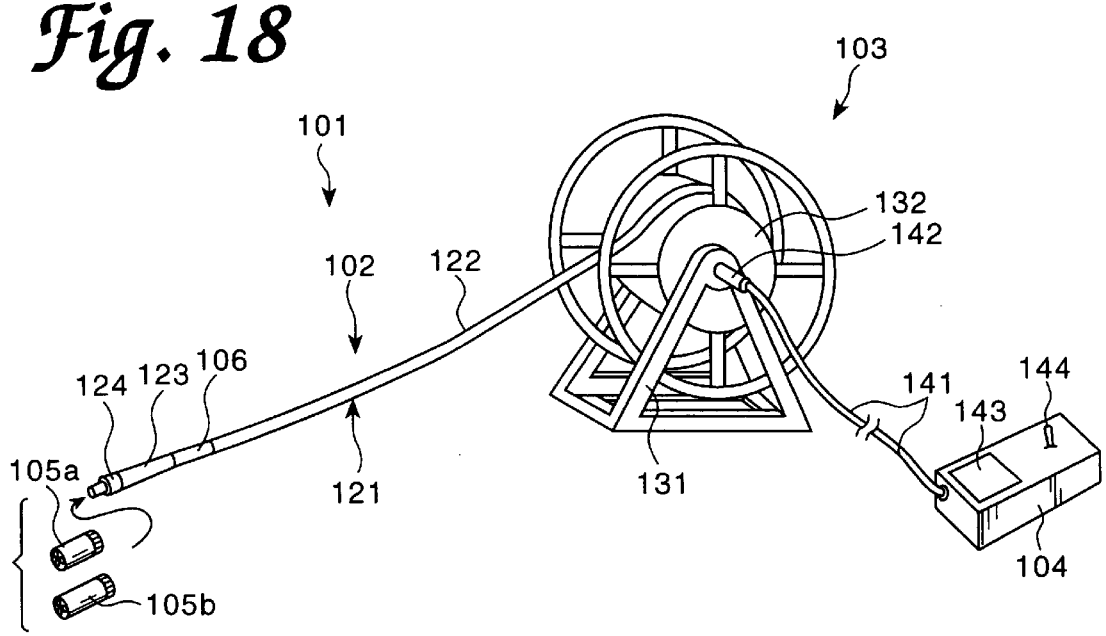
FIG. 18 illustrates a general configuration of an endoscope apparatus according to a third embodiment of the invention.

As shown in FIG. 18, an endoscope apparatus 101 according to the third embodiment is constituted of the following components. An industrial endoscope 102 has, for instance, a long, flexible insertion portion 121. A drum device 103 has a drum portion 132 that is rotatable with respect to a stand 131 and on which the insertion portion 121 of the industrial endoscope (hereinafter referred to as "endoscope") 102 is wound. A controller 104 is connected to the proximal end of an elongate electric cable 141 that is detachably connected to the drum device 103. The controller 104 has a manipulation means and an observation means.

The insertion portion 121 of the endoscope 102 consists of the following components. The proximal end portion of a soft, flexible tube 122 is attached to the drum portion 132. A curving portion 123 (described later) is provided adjacent to the tip side portion of the flexible tube 122 and is so constructed as to be curved to a desired direction. A tip hard portion 124 is provided adjacent to the tip-side portion of the curving portion 123 and incorporates a solid-state imaging device as an observation optical system, such as a charge coupled device (hereinafter abbreviated as "CCD"). The tip hard portion 124 is so constructed that plural kinds (two in FIG. 18) of tip adaptors 105a and 105b for converting the viewing angle or the viewing direction can be detachably mounted thereon. These tip adaptors 105a and 105b have different lengths, that is, different hard portion lengths.

Figure 19:
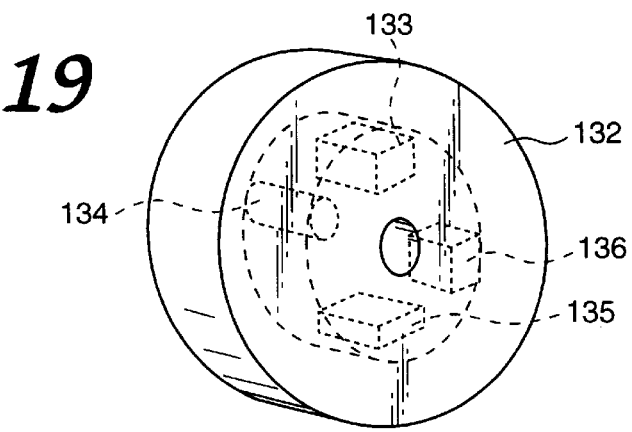
FIG. 19 illustrates a general configuration of a drum portion shown in FIG. 18.

As shown in FIG. 19, the following components are provided inside the drum portion 132. A camera control unit (hereinafter abbreviated as "CCU") 133 has an image processing circuit for generating a TV signal based on an image that is picked up by the CCD, a timing generation circuit for generating timing signals for driving the CCD, and other circuits. An actuator section 134 constitutes a curving means. A control circuit 136 controls the curving state of the curving portion 123 based on an instruction signal that is sent from the controller 104. A battery 136 serves as a power supply section for the CCD, the actuator section 134, and the control circuit 135. The CCU 133, the actuator section 134, the control circuit 135, and the battery 135 are so constructed as to be given balance weights for optimizing the weight balance of the drum portion 132 in consideration of its balance of rotation.

The tip portion of the electric cable 141 of the controller 104 is provided with a connector 142 that is detachable from a connector connecting portion (described later) provided at the rotation center of the drum portion 132. The controller 104 is also provided with a LCD monitor 143 for displaying an endoscope image that is picked up by the CCD and a joy stick 144 to be manipulated in curving the curving portion 123 to a desired direction.

The endoscope 102 will be described first.

Figure 20:
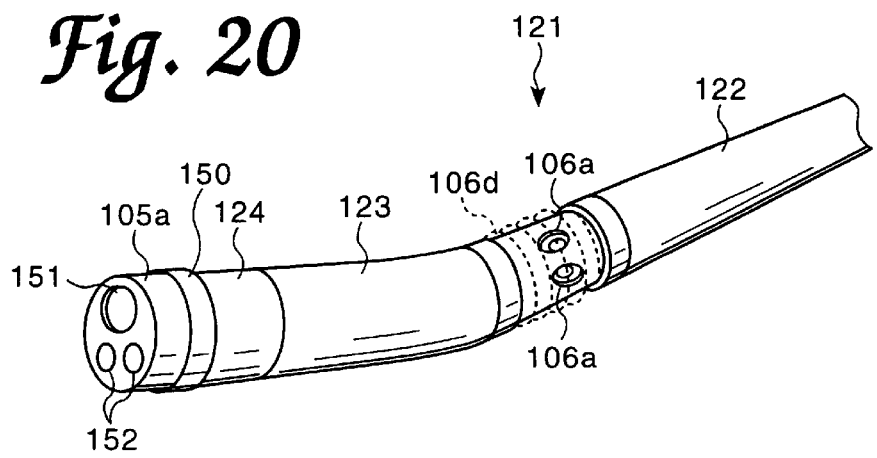
FIG. 20 is a perspective view showing the tip-side portion of an insertion portion shown in FIG. 18.

As shown in FIG. 20, for example, the tip adaptor 105a having an observation lens cover 151 that constitutes one observation window and illumination lens covers 152 that constitute two illumination windows is connected to the tip face of the tip hard portion 124. A flexible tube front mouth piece 106 is provided between the flexible tube 122 and the curving portion 123. Two metal contacts 106a are provided on the outer circumferential surface of the flexible tube front mouth piece 106.

A tip-side structure of the insertion portion 121 will be described below with reference to FIG. 21.

The flexible tube 122 has a three-layer structure including, in order from the outside, an impregnated resin layer 122a, a metal mesh layer 122b, and a metal spiral tube 122c, and is thus rendered flexible.

The generally pipe-shaped flexible tube front mouth piece 106 is provided on the tip side of the flexible tube 122. The metal contacts 106a provided on the flexible tube front mouth piece 106 are a cathode metal contact 106n and an anode metal contact 106p. The metal contacts 106n and 106p are connected to the ends of electric cables 106b corresponding to the characteristics of the metal contacts 106n and 106p, respectively. The metal contacts 106n and 106p are provided on the flexible tube front mouth piece 106 through non-conductive collars 106c. A non-conductive coil spring 106d is provided on the outer circumferential surface of the flexible tube front mouth piece 106 so as to protect the metal contacts 106n and 106p.

One end portion of a resin cover made of synthetic rubber that is an elastic member constituting the curving portion 123 covers the tip portion of the flexible tube front mouth piece 106, and the other end portion of the resin cover 125 covers the proximal end portion of the tip hard portion 124.

The resin cover 125 is fixed to the flexible tube front mouth piece 106 and the tip hard portion 124 in an integral manner by means of a thread-wound bonding portions (not shown) that are provided on both end portions of the resin cover 125. Thus, the resin cover 125 bridges the flexible tube front mouth piece 106 and the tip hard portion 124 with a given space provided in between. Instead of the resin cover 125, a tubular elastic member made of a material that is high in both flexibility and straight extendability, such as a super elastic alloy (Ni—Ti alloy), may be used.

One end portions of manipulation wires 126 as wire members that constitute, together with the resin cover 125, the curving portion 123 are connected to the tip hard portion 124. The manipulation wires 126 are wire members made of a Ni—Ti type alloy that exhibits a super elastic characteristic and is generally called a super elastic alloy. The manipulation wires 126 extend through the flexible tube front mouth piece 106 and the flexible tube 122, and the other end portions of the manipulation wires 126 are connected and fixed to the actuator section 134 as the curving means for moving the manipulation wire 126 in the longitudinal direction of the insertion portion 121. The actuator section 134 is provided in the drum portion 132. In the third embodiment, three manipulation wires 126 are used, an arrangement of which will be described later with reference to FIG. 23.

To detect a curving direction, each of the manipulation wires 126 is provided, in the curving portion 123, with a sensor 126a such as a strain gauge. Curving state detection signals produced by the respective sensors 126a are transmitted by signal transmission lines 126b extending from the respective sensors 126a and input to the control circuit 135 in the drum portion 132.

The tip hard portion 124 is provided with a CCD 127 that constitutes an observation optical system and contact electrodes 128 as second electrical contacts to serve as cathode and anode contacts for supplying illumination power to, for instance, an LED device (hereinafter referred to as "LED") as a light-emitting element that constitutes an illumination optical system (described later).

The CCD 127 has a driver circuit 127a for driving it, a preamplifier 127b for amplifying an electrical signal produced through photoelectric conversion of an image formed on the imaging surface of the CCD 127, and other circuits. A signal cable 129 for signal exchange extends from the driver circuit 127a and the preamplifier 127b to the drum portion 132, going through the flexible tube front mouth piece 106 and the flexible tube 122. The proximal end of the signal cable 129 is connected to the CCU 133 that is provided in the drum portion 132.

On the other hand, one ends of electric wires 128a corresponding to the characteristics of the above-mentioned contact electrodes 128 are connected to those electrodes, respectively. The electric wires 128a goes through the insertion portions 121 and the other ends of electric wires 128a are connected to the battery 136 which is provided in the drum portion 132.

The tip portion of the tip hard portion 124 is provided with the tip adaptor 105a having an observation lens cover 151 and an objective lens 153 that constitute the observation optical system and an LED 154 that emits illumination light. The tip adaptor 105a is connected and fixed to the tip of the insertion portion 121 through a rotary ring 150 whose inner circumferential surface is formed with a female thread portion that engages a male thread portion (not shown) formed on the outer circumferential surface of the tip hard portion 124. The rotary ring 150 is provided with a water-tight member (not shown) for preventing dust, water, or the like from entering the inside of the endoscope 102 through the connecting portion of the tip adaptor 105a and the tip hard portion 124.

The LED 154 which is provided in the tip adaptor 105a has a cathode terminal 154n and an anode terminal 154p that are opposed to the contact electrodes 128 provided in the tip hard portion 124. The optical axis of the LED 154 coincides with the viewing direction of the observation optical system.

Figure 22A:
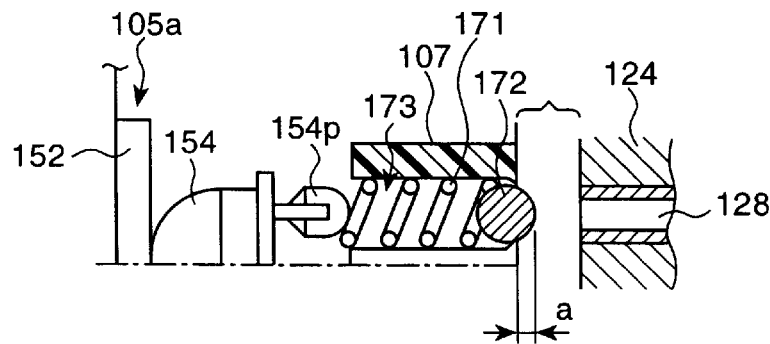
FIGS. 22(*a*) and 22(*b*) illustrate the structure and operation of a conduction holder that is provided in a tip adaptor shown in FIG. 21.

The tip adaptor 105a is provided with a conduction holder 107 that is made of an insulative material. The conduction holder 107 is formed with fitting through-holes 173 which are fitted with conductive, coil-shaped compression springs 171 and metal balls 172 for electrical conduction between the contact electrodes 128 and the cathode and anode terminals 154n and 154p of the LED 154. As shown in FIG. 22(a), when the fitting through-holes 173 are fitted with the metal balls 172 and the compression springs 171, the cathode and anode terminals 154n and 154p contact the end faces of the respective compression springs 171. Thus, first electrical contacts are formed. In a state that the tip adaptor 105a is not attached to the tip hard portion 124, urging force of the compression strings 171 causes the balls 172 (provided on theproximalside) to project from the proximal face by a dimension a.

Figure 22B:
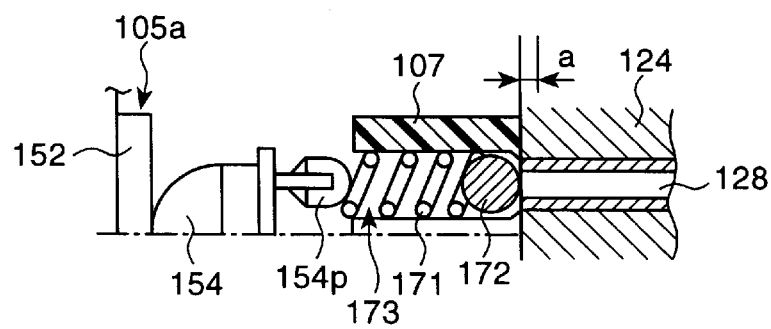

On the other hand, as shown in FIG. 22(b), in a state that the tip adaptor 105a is attached to the tip hard portion 124, the metal balls 172 being urged by the compression springs 171 are brought in contact with the tip faces of the respective contact electrodes 128. As a result, the LED 154 is turned on being supplied with illumination power from the battery 136 via the electric wires 128a, the contact electrodes 128, the metal balls 172, the compression springs 171, and the cathode and anode terminals 154n and 154p. Since the urging force of the compression springs 171 causes the metal balls 172 to be always pressed against the tip faces of the respective contact electrodes 128, reliable conduction can be obtained irrespective of the manipulation on the endoscope 102.

Figure 23:
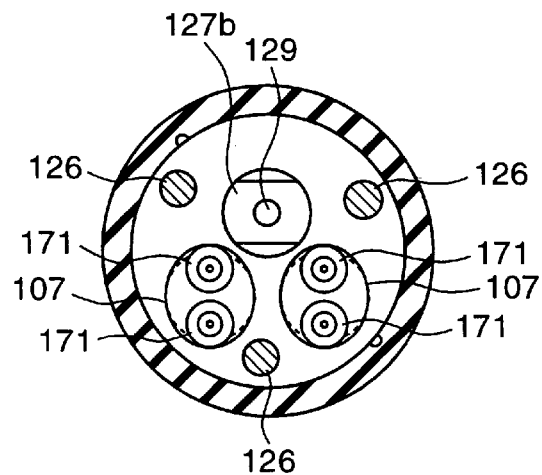
FIG. 23 is a sectional view taken along line D—D in FIG. 21.

As shown in FIG. 23, the three manipulation wires 126 which are part of the curving portion 123 are provided in equilateral triangle form and fixed to the tip hard portion 124 at positions close to its outer circumferential surface to secure sufficient internal space, so as not to butt against the contact electrodes 128 for supplying power to the LED 154.

The three manipulation wires 126, which are fixed to the tip hard portion 124 and extend to the drum portion 132, are arranged such that at least one of a plurality of planes each formed by an arbitrary pair of the three manipulation wires 126 does not include the central axis of the insertion portion 121(curving portion).

Therefore, when at least one of the three manipulation wires 126 is moved by the actuator section 134, the remaining manipulation wire(s) 126 that is not moved by the actuator section 134 resists the moving manipulation wire 126 and is curved toward the moving manipulation wire 126.

Next, the drum device 103 will be described.

Figure 24:
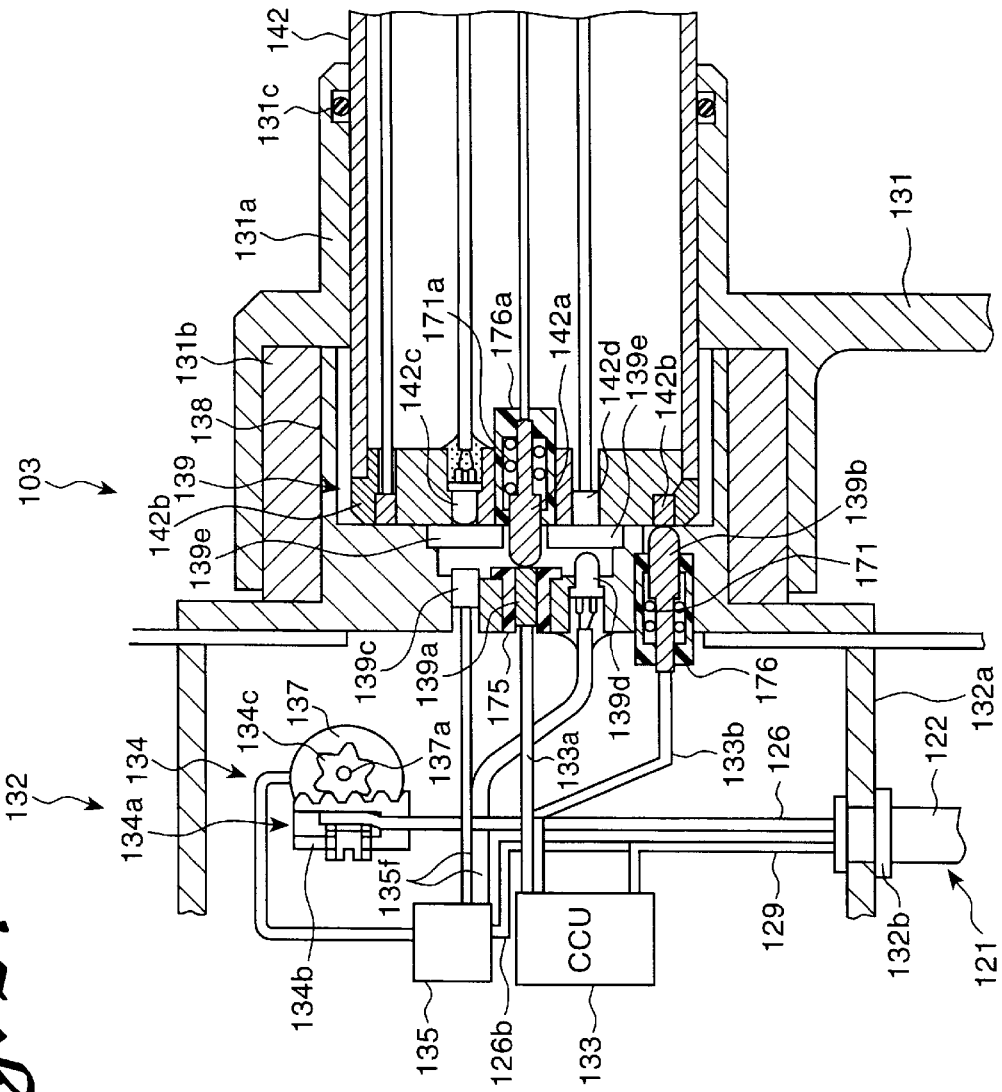
FIG. 24 illustrates a connection relationship between the drum portion shown in FIG. 18 and connectors and a structure of an actuator section that is provided in the drum portion.

As shown in FIG. 24, the proximal end portion of the flexible tube 122 which is part of the insertion portion 121 is connected to a connection member 132b that is provided on a winding surface 132a of the drum portion 132. Each of the manipulation wires 126 goes through the curving portion 123, the flexible tube front mouth piece 106, and the flexible tube 122, and reaches the inside of the drum portion 132. One end portion of each manipulation wire 126 is connected to a rack 134b a rack-pinion portion 134a that constitutes the actuator 134. The rack 134b advances or retreats in accordance with the rotation of a pinion 134c, which is rotated by a motor 137. The motor 137 is fixed to the inside of the drum portion 132.

Figure 25:
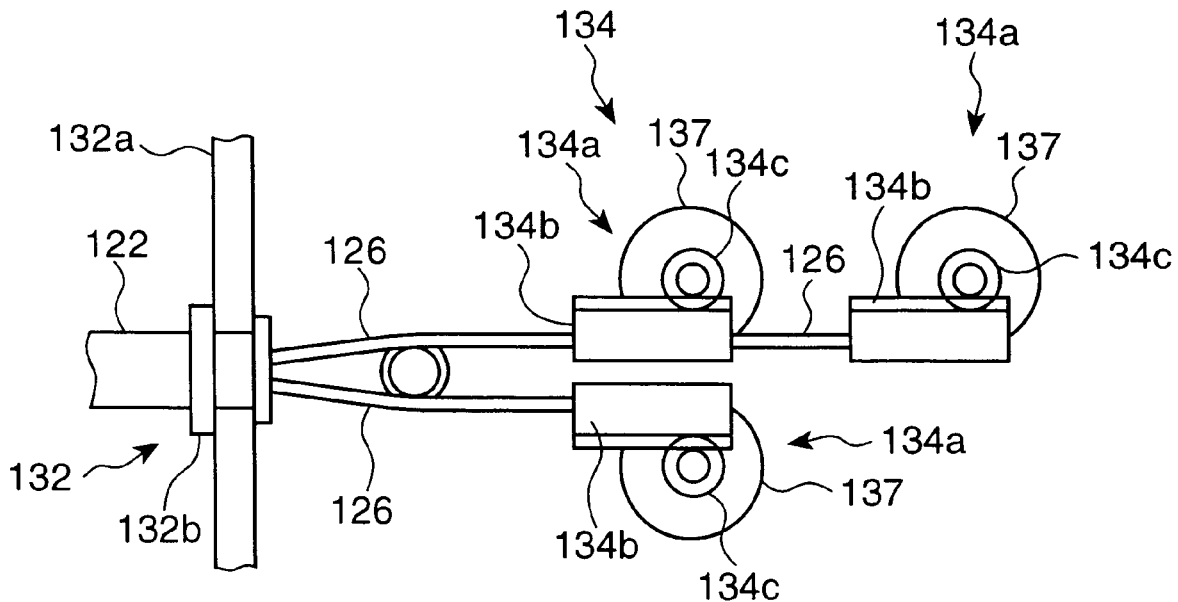
FIG. 25 illustrates a specific structure of the actuator section shown in FIG. 24.

As shown in FIG. 25, three rack-pinion portions 134a are provided in the actuator section 134 so as to correspond to the three respective manipulation wires 126 which are inserted in the insertion portion 121. The end portion of each manipulation wire 126 is connected to the rack 134b of each rack-pinion portion 134a.

The manipulation wires 126 advance or retreat independently of each other in accordance with the operations of the respective rack-pinion portions 134a. By causing the respective rack-pinion portions 134a to advance or retreat by properly controlling their operations, the manipulation wires 126 that are fixed to the respective racks 134b advance or retract accordingly, whereby the curving portion 123 is curved to a desired direction.

An alternative configuration is possible in which the curving portion 123 is curved by pushing at least one of the manipulation wires 126 from the initial position where a curve is canceled to the curving portion side, and the curve thus produced is canceled by returning the manipulation wire 126 to the initial position.

As shown in FIG. 24, the end portions of the signal transmission lines 126b and the signal cable 129 that go through the insertion portion 121 and reach the inside of the drum portion 132 are connected to the control circuit 135 and the CCU 133, respectively, which are provided in the drum portion 132.

Figure 26:
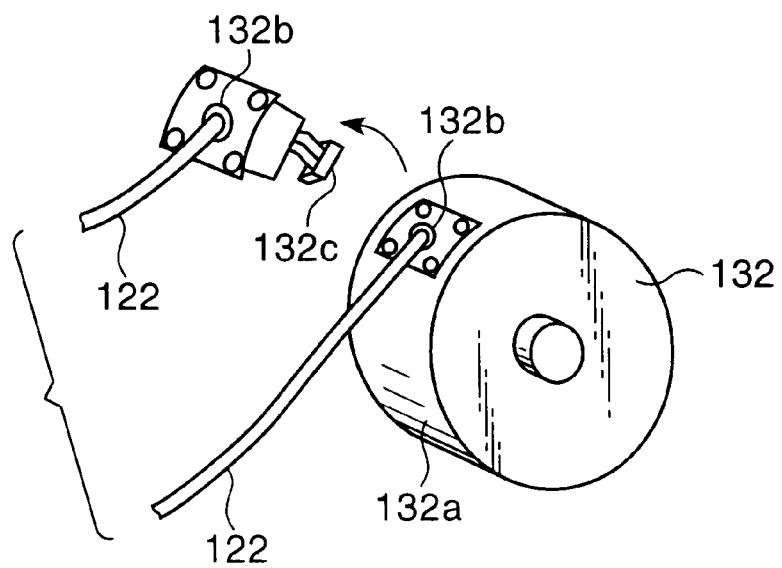
FIG. 26 illustrates a specific example of a manner of attaching the inserting portion to the drum portion, both shown in FIG. 18.

As for a specific manner of attaching the insertion portion 121 of the endoscope 102 to the drum portion 132, reference is made to FIG. 26. That is, as shown in FIG. 26, the connection member 132b to which the proximal end portion of the flexible tube 122 (insertion portion 121) is connected can be detachably fixed to the winding surface 132a of the drum portion 132 with vises.

The connection member 132b is provided with a connector 132c that is electrically connected to the CCU 133 and the control circuit 135 (and the battery 136) which are provided in the drum portion 132. By connecting the connector 132c of the connection member 132b to a corresponding connector in the drum portion 132, the signal transmission lines 126b and the signal cable 129 which are inserted in the insertion portion 121 are connected to the control circuit 135 and the CCU 133. The connection between the insertion portion 121 and the drum portion 132 is completed by fixing the connection member 132b to the winding surface 132a with vises after the connector 132c is connected to the corresponding connector.

To obtain a rotation speed that is reduced from the rotation speed of the motor 137, a reduction gear mechanism may be provided between a rotary shaft 137a of the motor 137 and the pinion 134c.

Next, a description will be made of a connection relationship between the controller 104 and the control circuit 135 and the CCU 133.

As shown in FIG. 24, a connector receptacle 131a incorporating a bearing portion 131b projects from a side face of the stand 131 of the drum device 103. A shaft portion 138, which projects from aside face central portion of the drum portion 132 and has a plurality of contact portions on the bottom face of a connector connecting portion 139, is attached to the bearing portion 131b of the connector receptacle 131a so as to be rotatable with respect to the stand 131.

The bottom face of the connector connecting portion 139 of the shaft portion 138 which projects from the drum portion 132 is provided with a video signal contact electrode 139a to which a video signal line 133a extending from the CCU 133 is connected and a ground (or GND) terminal 139b to which a ground line 133b is connected, as well as with communication photodiodes 139c and communication LEDs 139d that are connected to communication cables 135f for bidirectional communication extending from the control circuit 135.

The video signal contact electrode 139a to which the video signal line 133a is connected is provided in a non-conductive first holder 175 that is located on the rotation central axis of the drum portion 132. On the other hand, the GND terminal 139b to which the ground line 133b is connected is accommodated in a non-conductive second holder 176 that is located at a position distant from the video signal contact electrode 139a and close to the outer circumferential surface of the connector connecting portion 139. The GND terminal 139b is always urged sideways and outward by a compression spring 171 that is provided in the second holder 176. Diffusion plates 139e are disposed in front of the communication photodiodes 139c and the communication LEDs 139d.

On the other hand, the tip face of a connector 142 that is inserted in the connector receptacle 131a and connected to the connector connecting portion 139 is provided with a video signal connection terminal 142a, a GND contact electrode 142b, communication LEDs 142c, and communication photodiodes 142d so as to be opposed respectively to the video signal contact electrode 139a, the GND terminal 139b, the diffusion plates 139c that are disposed in front of the communication photodiodes 139c and the communication LEDs 139d.

The video signal connection terminal 142a is accommodated in a non-conductive third holder 176a that is sealed and fixed with a filler or the like at the center of the connector 142. The video signal connection terminal 142a is always urged sideways and outward by a compression spring 171a that is provided in the third holder 176a. The communication LEDs 142c and communication photodiodes 142d are sealed and fixed with a filler or the like so as to be opposed respectively to the communication photodiodes 139c and the communication LEDs 139d which are provided in the connector connecting portion 139. Further, the GND contact electrode 142b is formed in ring-like form on the tip face of the connector 142 so as to provide reliable conduction with the GND terminal 139b which is located close to the outer circumferential surface of the connector connecting portion 139.

With the above configuration, light that is emitted from the communication LEDS 142c based on a curving instruction signal that is produced as a result of a manipulation on the joy stick 144 provided on the controller 104 is diffused by the diffusion plates 139e of the connector connecting portion 139, reaches the photodiodes 139c, and finally transmitted to the control circuit 135 via the communication cable 135f. Even if the connector 142 is attached to the connector connecting portion 139 in any circumferential positional relationship with the latter, emitted light is transmitted, as a curving instruction signal, to the control circuit 135 in a reliable manner by virtue of the use of a plurality of communication LEDs 142c and the diffusion effect of the diffusion plates 139e.

Since the video signal connection terminal 142a to contact the video signal contact electrode 139a which is connected to the video signal line 133a extending from the CCU 133 and the GND terminal 139b to contact the GND contact electrode 142b provided in the connector 142 are always pressed by the urging force of the compression springs 171a and 171 to as to contact the contact electrodes 139a and 142b, respectively, signal exchange can be performed in such a state that reliable conduction is established between the terminals 139b and 142a and the contact electrodes 139a and 142b.

An O-ring 131c is provided on the inner circumferential surface of the connector receptacle 131a on its mouth side to prevent entrance of dust, water, or the like into the inside of the connecting portion as well as falling of the connector 142 from the connector receptacle 131a.

Figure 27:
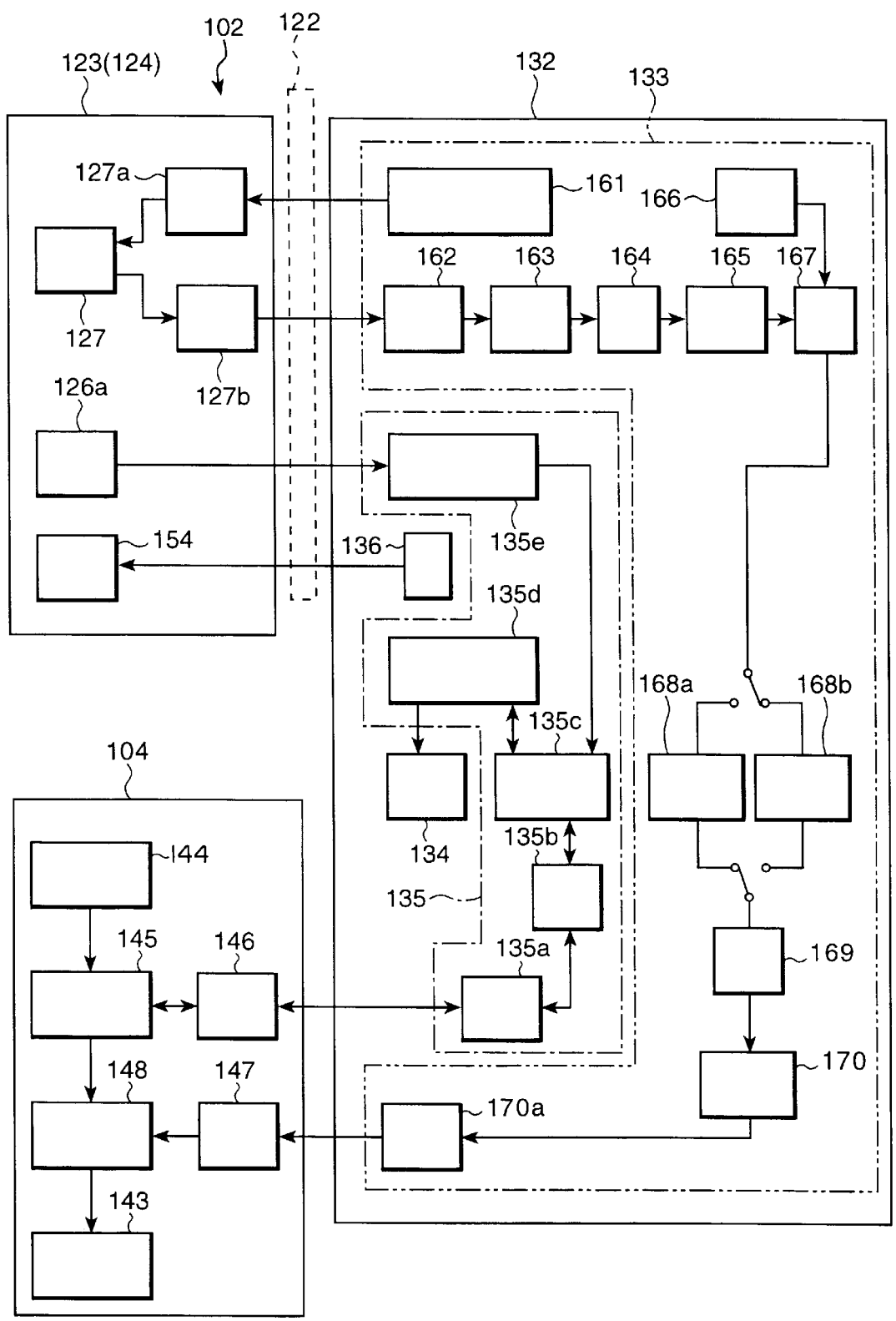
FIG. 27 is a block diagram showing a general configuration of the endoscope apparatus of FIG. 18.

The operation of the above-configured endoscope apparatus 101 will be described with reference to a block diagram of FIG. 27.

The tip hard portion 124 of the endoscope 102 is provided with the LED 154 for illuminating a part to be observed, the CCD 127 for imaging the part to be observed that is illuminated by the LED 154, the driver circuit 127a for driving the CCD 127, and the preamplifier 127b for amplifying an electrical signal that is produced through photoelectric conversion of an image formed on the imaging surface of the CCD 127. The sensors 126a for detecting curving states of the respective manipulation wires 126 are provided at intermediate positions, in the curving portion 123, of the manipulation wires 126 whose tips are fixed to the tip hard portion 124 and which extend to the actuator section 134.

The drum portion 132 of the drum device 103 incorporates the CCU 133 having the image processing circuit for producing a video signal from an electrical signal supplied from the CCD 127 and other circuits, the actuator section 134 for advancing or retreating the manipulation wires 126, the control circuit 135 for controlling, for instance, a curving state of the curving portion 123, and the battery 136 as a power supply.

The LED 154 is turned on being supplied with power from the battery 136 when the flexible tube 122 constituting the insertion portion 121 is connected and fixed to the drum portion 132.

The controller 104 is provided with the joy stick 144 as a manipulation switch, A CPU 145 for converting a movement of the joy stick 144 into a curving instruction signal, a communication circuit 146 for supplying the thus-produced curving instruction signal to the control circuit 135, a TV signal receiving circuit 147 as a receiving section of a TV signal that is transmitted from the CCU 133, the LCD monitor 143 as a TV monitor, and a superimposer 148 for causing the LCD monitor 143 to display image information and text information.

The CCD driver circuit 127a which is provided in the tip hard portion 124 is driven by drive signals that are output from a timing generation circuit 161 that is provided in the CCU 133.

An electrical signal obtained by amplification, by the preamplifier 127b, of a signal that is produced based on an image formed on the imaging surface of the CCD 127 is transmitted to an image processing circuit of the CCU 133. In the image processing circuit, the received electrical signal is subjected to known processing in the clamping circuit 162 and a sample hold circuit 163, amplified by a amplifier (not shown), and then A/D-converted by an A/D conversion circuit 164. Image data produced by the A/D conversion is input to a memory 165. Based on the image data, a DSP (digital signal processor) 167 produces a video signal of a given format according to a program stored in a DSP ROM 166. After passing through a first frame memory 168a or a second frame memory 168b, the video signal is D/A-converted by a D/A conversion circuit 169 and then input to an encoder 170, which produces a TV signal to be output to the external apparatus. The TV signal is output to the TV signal receiving circuit 147 of the controller 104 via a TV signal transmission circuit 170a.

In summary, an image that is picked up by the CCD 127 is converted into an electrical signal, which is amplified by the preamplifier 127b and then transmitted to the CCU 133. Based on the received electrical signal, the CCU 133 produces a TV signal, which is output to the TV signal receiving circuit 147 of the controller 104 via the TV signal transmission circuit 170a. The TV signal is then displayed on the LCD monitor 143 via the superimposer 148.

When a curving manipulation on the curving portion 123 is made by manipulating the joy stick 144 of the controller 104, a curving instruction signal representing a movement of the joy stick 144 is supplied from the joy stick 144 to a control CPU 135b via the CPU 145, the communication circuit 146, and a communication circuit 135a of the control circuit 135 which is provided in the drum portion 132.

Upon reception of the curving instruction signal, the control CPU 135b controls, via a curving control circuit 135c, a curving driver circuit 135d so that the curving driver circuit 135d supplies a drive signal to a related motor 137 of the actuator section 134, to start driving the motor 137. As a result, the pinion 134c is rotated by a specified amount in a specified direction, the rack 134b is moved accordingly, and finally the corresponding manipulation wire 126 is moved in the specified direction.

As a result, the remaining, i.e., unmoved, manipulation wire(s) 126 resists the moving manipulation wire 126, to establish a state that the tip hard portion 124 is pulled toward the flexible tube front mouth piece 106. Thus, the manipulation wires 126 are warped and the curving portion 123 is curved to one of the directions indicated by arrows in FIG. 28.

Figure 28:
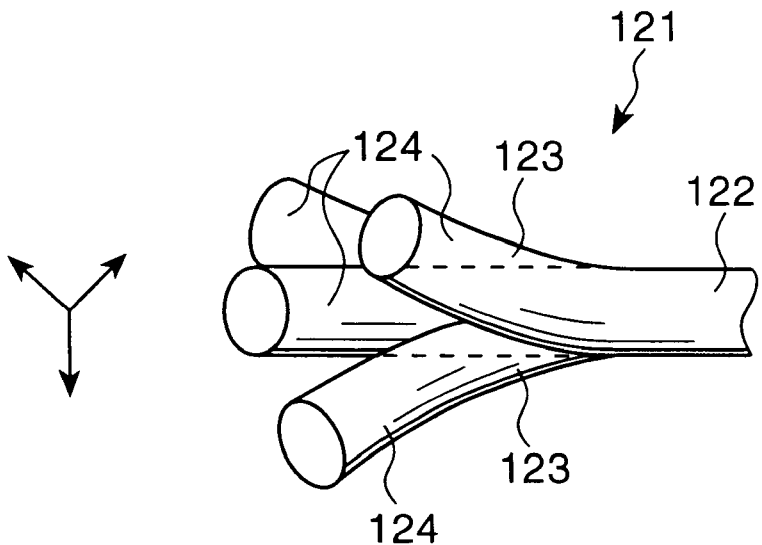
FIG. 28 illustrates a curving state of the curving portion shown in FIG. 18.

When the curving portion 123 starts to curve as shown in FIG. 28, stress amounts are detected by the sensors 126a which are provided on the respective manipulation wires 126, and curving state detection signals representing the respective stress amounts are transmitted to a sensor signal receiving circuit 135e of the control circuit 135. The received curving state detection signals are supplied to the control CPU 135b via the curving control circuit 135c. After the curving state detection signals are compared with the curving instruction signal that is supplied from the joy stick 144, the curving driver circuit 135d again outputs a drive signal to the actuator section 134, which advances or retreats the respective manipulation wires 126 so that the curving portion 123 is curved in the direction according to the instruction from the joy stick 144.

As described above, where the distal end portion of the three manipulation wires 126 each made of a super elastic alloy are fixed to the tip hard portion 124 which is located at the tip of the insertion portion 121, the three manipulation wires 126 are arranged so that at least one of planes each of which is formed by arbitrarily selected two of the three manipulation wires 126 does not include the central axis of the tip hard portion 124 and the curving portion 123 which constitute the insertion portion 121, and the curving mechanism is constructed by connecting the proximal ends of the respective manipulation wires 126 to the rack-pinion portions 134a which advance or retreat the respective manipulation wires 126. Thus, by properly adjusting the movements of the respective manipulation wires 126 for the respective rack-pinion portions 134a, the curving portion 123 can be curved to a desired direction.

The sensors 126a for detecting curving states of the three respective manipulation wires 126 are provided thereon at the intermediate positions, in the curving portion 123, of the respective manipulation wires 126, and curving state detection signals that are output from the respective sensors 126a are supplied to the curving control circuit 135c of the control circuit 135. The curving state detection signals are compared with a curving instruction signal that is supplied from the joy stick 144. Based on comparison results, a drive signal for controlling the curving state of the curving portion 123 is newly output to the actuator section 134 from the curving driver circuit 135d, to advance ot retreat the respective manipulation wires 126. Thus, the curving portion 123 can be curved in a reliable manner to the direction according to the instruction from the joy stick 144.

Further, by virtue of the fact that the curving portion 123 and the curving mechanism are formed by using the three manipulation wires 126, wider space can be secured in the curving section 123 than in the conventional curving portion that is constituted of a plurality of curving blocks and a manipulation wire for curving a curving tube that is formed by the plurality of curving blocks. Since sufficient space for insertion of the internal components other than the curving mechanism is secured, it is no longer necessary to reduce the diameters of the respective internal components and, on the other hand, it becomes possible to reduce the diameter of the endoscope insertion portion.

The LED 154 is provided in the tip adaptor (105a), and illumination light is emitted from the LED 154 that is supplied with power from the battery 136 of the drum portion 132 when the flexible tube that constitutes the proximal portion of the insertion portion 121 is connected to the drum portion 132. In this manner, a part to be inspected can always be illuminated with a necessary amount of light. This eliminates problems of optical loss due to long extension of light guide fibers that are usually used as an illumination means and reduction or insufficiency in light quantity due to optical loss at the connection face with a tip adaptor. Further, it is no longer necessary to increase the fiber diameter or use expensive fibers having high transmission efficiency to efficiently transmit illumination light from a very distant light source device to a part to be observed. This realizes thinning of the endoscope and an inexpensive configuration.

By virtue of the fact that the video signal contact electrode 139a to which the video signal line 133a extending from the CCU 133 is connected and the video signal connection terminal 142a which is provided in the connector 142 are located on the rotation central axis of the drum portion 132, a failure in conduction between the video signal contact electrode 139a and the video signal connection terminal 142a due to the rotation of the drum portion 132 can be prevented in a reliable manner.

Further, the metal balls 172 which are provided in the tip adaptor (105a) are always pressed against the tip faces of the contact electrodes 128 by the urging force of the compression springs 171, and the video signal connection terminal 142a and the ground terminal 139b are always pressed against the video signal contact electrode 139a and the ground contact electrode 142b by the urging force of the compression springs 171a and 171, respectively. Therefore, reliable conduction can be established between the metal balls 172 and the contact electrodes 128, between the video signal connection terminal 142a and the video signal contact electrode 139a, and between the ground terminal 139b and the ground contact electrode 142b.

Although in the third embodiment the LED 154 is used as the illumination means, a similar configuration may be obtained by replacing the LED 154 with a lamp. Further, like the first embodiment, a grinding means comprising the grinding stone 18, the rotational force transmission member 35, and the like may be provided in the insertion portion 121.
Embodiment 4

FIGS. 29–32 relate to a fourth embodiment of the invention.

The configuration of an endoscope 102 will be described first.

Figure 29:
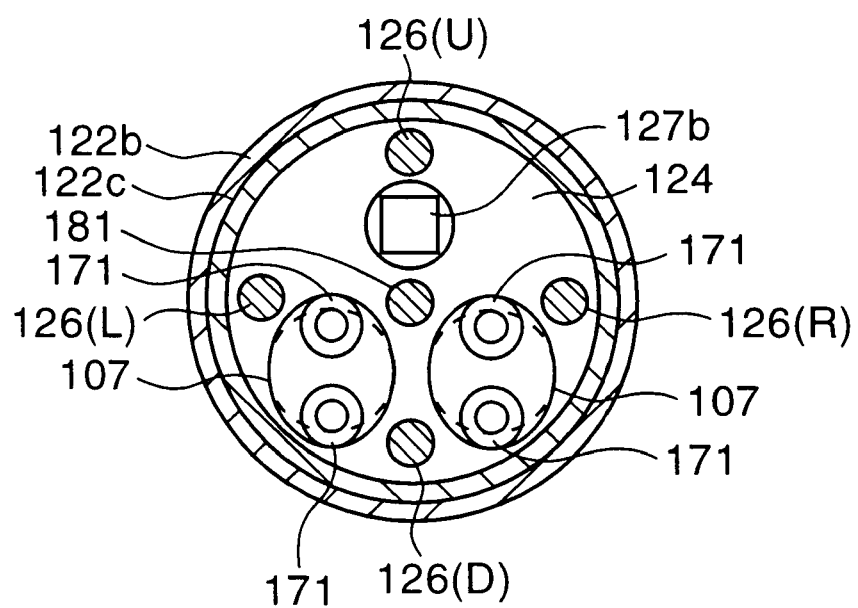
FIG. 29 is a sectional view of a curving portion of an endoscope having four manipulation wires and one interval maintaining wire according to a fourth embodiment of the invention.

As shown in FIG. 29, in the fourth embodiment, four manipulation wires 126 are used, that is, the number of manipulation wires 126 is increased by one from the case of the third embodiment. The four manipulation wires 126 are fixed to the tip hard portion 124 at four equally divided positions close to its outer circumferential surface so as to serve as up, down, right, and left manipulation wires 126U, 126D, 126R, and 126L.

One end of an interval maintaining wire 181 as a wire rod for keeping the interval of the curving portion 123 at a given value is fixed to the tip hard portion 124 at a position approximately on the central axis. The other end of the interval maintaining wire 181 is fixed to the flexible tube front mouth piece 106 at a position approximately on the central axis.

Further, the resin cover 125 which covers the curving portion 123 in the third embodiment is replaced by a composite tube of a metal mesh tube 122b and a metal spiral tube 122c that are provided concentrically. In the composite tube, either the metal mesh tube 122b or the metal spiral tube 122c may be provided outside.

Next, the structure of an actuator section 134 will be described.

Figure 30:
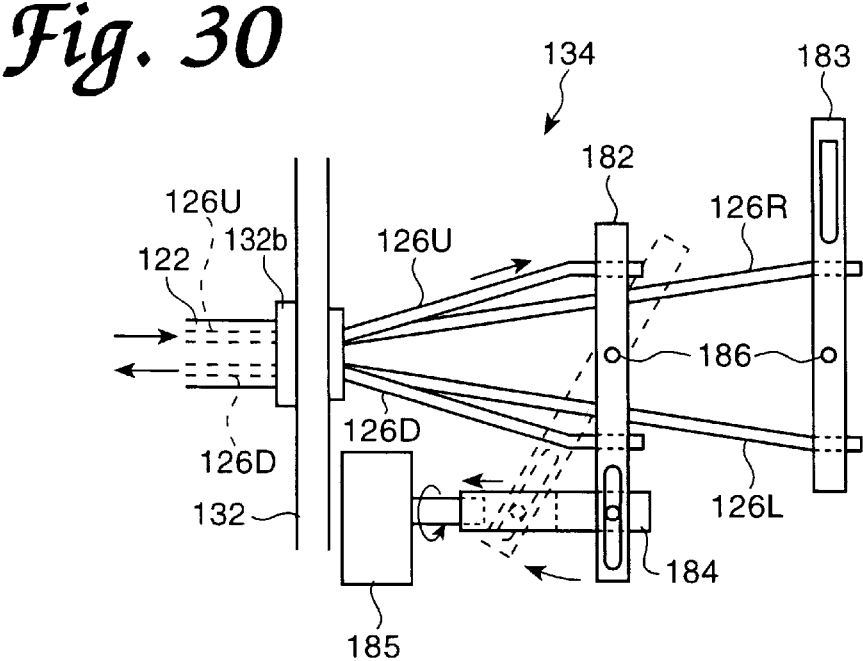
FIG. 30 illustrates a structure of a link mechanism that constitutes an actuator section of the endoscope of FIG. 29.

As shown in FIG. 30, the actuator section 134 of the fourth embodiment is constituted of a link mechanism portion having a top/bottom link bar 182 to which the up and down manipulation wires 126U and 126D are connected and a right/left bar 183 to which the right and left manipulation wires 126R and 126L are connected, screw-type linear driving members 184 that are respectively connected to the up/down link bar 182 and the right/left link bar 183, motors 185 for driving the respective screw-type linear driving members 184. In FIG. 30, the screw-type linear driving member 184 connected to the right/left link bar 183 and the motor 185 for driving it are omitted.

Figure 31:
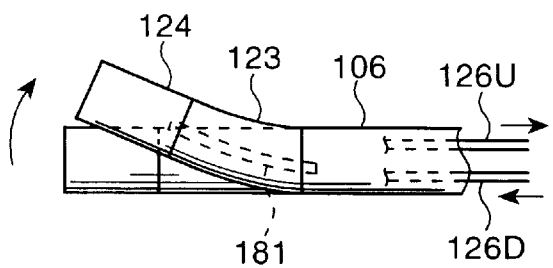
FIG. 31 illustrates action of the link mechanism of FIG. 30.

The link bar 182 which constitutes a up/down link mechanism portion is axially supported so as to be rotatable about a shaft 186 that is fixed to the inside of the drum portion 132. One end of the link bar 182 is connected to one end of the screw-type linear driving member 184 which is advanced or retreated by the motor 185. With this structure, for example, by rotating the motor 185 by a drive signal that is supplied from the curving driver circuit 135d, the link bar 182 which is connected to the screw-type linear driving member 184 from a position indicated by solid lines to a position indicated by broken lines. As a result, as shown in FIG. 31, the up manipulation wire 126U is pulled while the down manipulation wire 126D is pushed; that is, a pair of manipulation wires 126U and 126D are simultaneously subjected to a push/pull manipulation. As a result, the curving portion 123 is curved to the direction of the up manipulation wire 126U that is being pulled.

The structure relating to the right-left direction is not described because it is the same as the above-described structure relating to the up-down direction. The up and down manipulation wires 126U and 126D are fixed to the link bar 182 at positions that are equally distant from the shaft 186 as the supporting point. Similarly, the right and left manipulation wires 126R and 126L are fixed to the link bar 183 at positions equally distant from the shaft 186. Since the other structures of the third embodiment are the same as those of the third embodiment, descriptions therefor are omitted with the same parts and components given the same reference symbols.

Next, the operation of the above-configured endoscope apparatus will be described.

Figure 32:
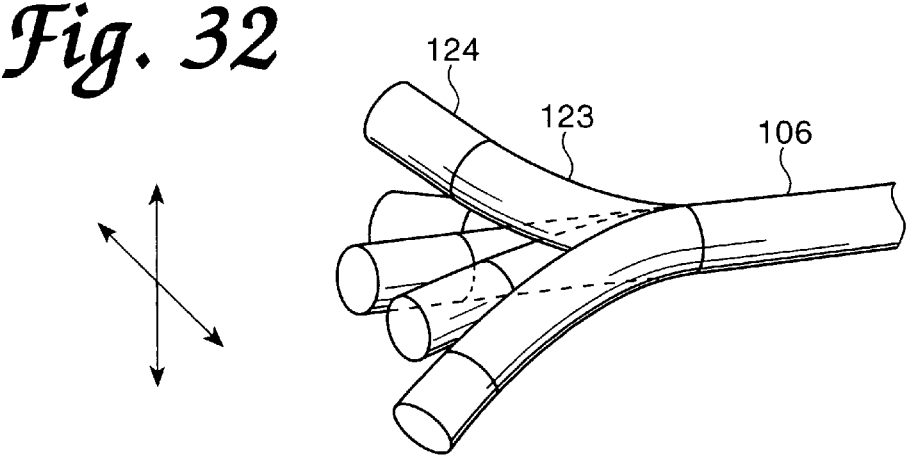
FIG. 32 illustrates a curving state of the curving portion in the fourth embodiment.

As in the case of the third embodiment, a curving instruction signal is supplied to the control CPU 135b by manipulating the joy stick 144. In response, the control CPU 135b controls, via the curving control circuit 135c, the curving driver circuit 135d so that the curving control circuit 135d supplies drive signals to the motors 185 corresponding to the up/down and right/left directions, respectively, whereby the motors 185 start rotating. As a result, the screw-type linear driving members 184 advance or retreat in specified directions, and the link bars 182 and 183 which are connected to the respective screw-type linear driving members 184 turn about the respective shafts 186. As a result, the up and down manipulation wires 126U and 126D which are connected to the link bar 182 and/or the right and left manipulation wires 126R and 126L move relatively to each other, whereby the position of the tip hard portion 124 with respect to the flexible tube front mouth piece 106 is changed. In this manner, the interval maintaining wire 181 is warped and the curving portion 123 can be curved freely in a desired direction as shown in FIG. 32.

As described above, the number of manipulation wires is increased and the interval maintaining wire 181 as the member for keeping the interval of the curving portion 123 at a given value is fixed to the tip hard portion 124 and the flexible tube front mouth piece 106. As the manipulation wires 126 are moved, the interval maintaining wire 181 is warped and the curving portion 123 is curved. In this manner, the curving control can be performed with high accuracy.

Further, since the interval of the curving portion 123 is kept at a given value by means of the interval maintaining wire 181, the curving portion 123 can be curved at a small radius of curvature and a curve angle can be maintained in a stable manner.

Although in the fourth embodiment the number of manipulation wires is increased, the curving portion 123 may be formed by using the interval maintaining wire 181 and two manipulation wires 126. Even in this case, it is possible to curve the curving portion 123 to a desired direction by properly setting the arrangement positions of the interval maintaining wire 181 and the manipulation wires 126. A plurality of interval maintaining wires 181 may be provided. Further, instead of increasing the number of link mechanisms as the number of manipulation wires 126 is increased, the number of rack-pinion portions may be increased as the number of manipulation wires 126 is increased. Further, instead of a compound tube comprising the metal mesh layer 122b and the metal spiral tube 122c, as shown in the second embodiment, the tip portion length adjustment member which comprises the plurality of blocks 61, 61a and 61b may be provided.
Embodiment 5

Figure 33:
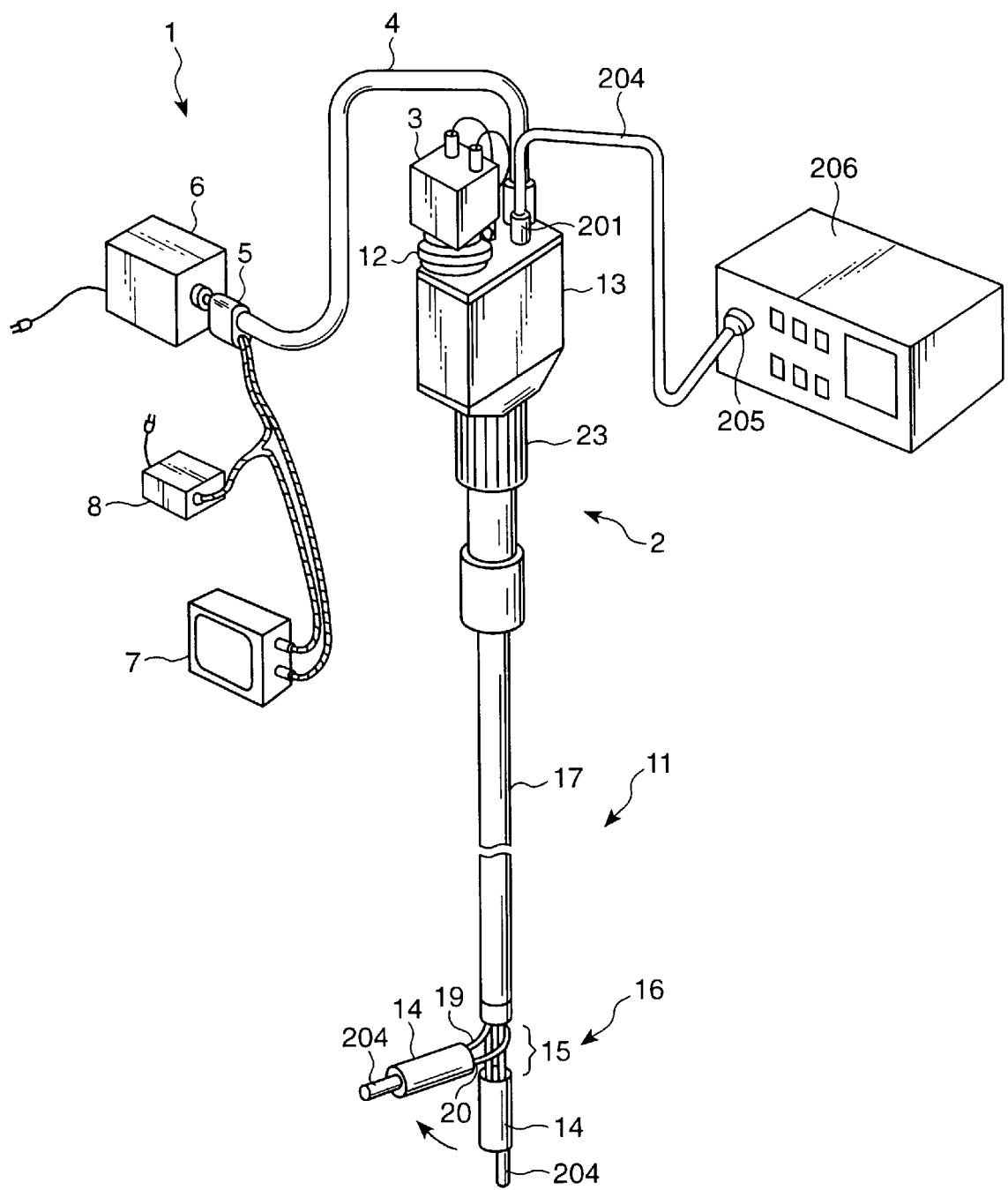
FIG. 33 shows the configuration of an industrial endoscope processing apparatus according to a fifth embodiment of the invention.
Figure 34:
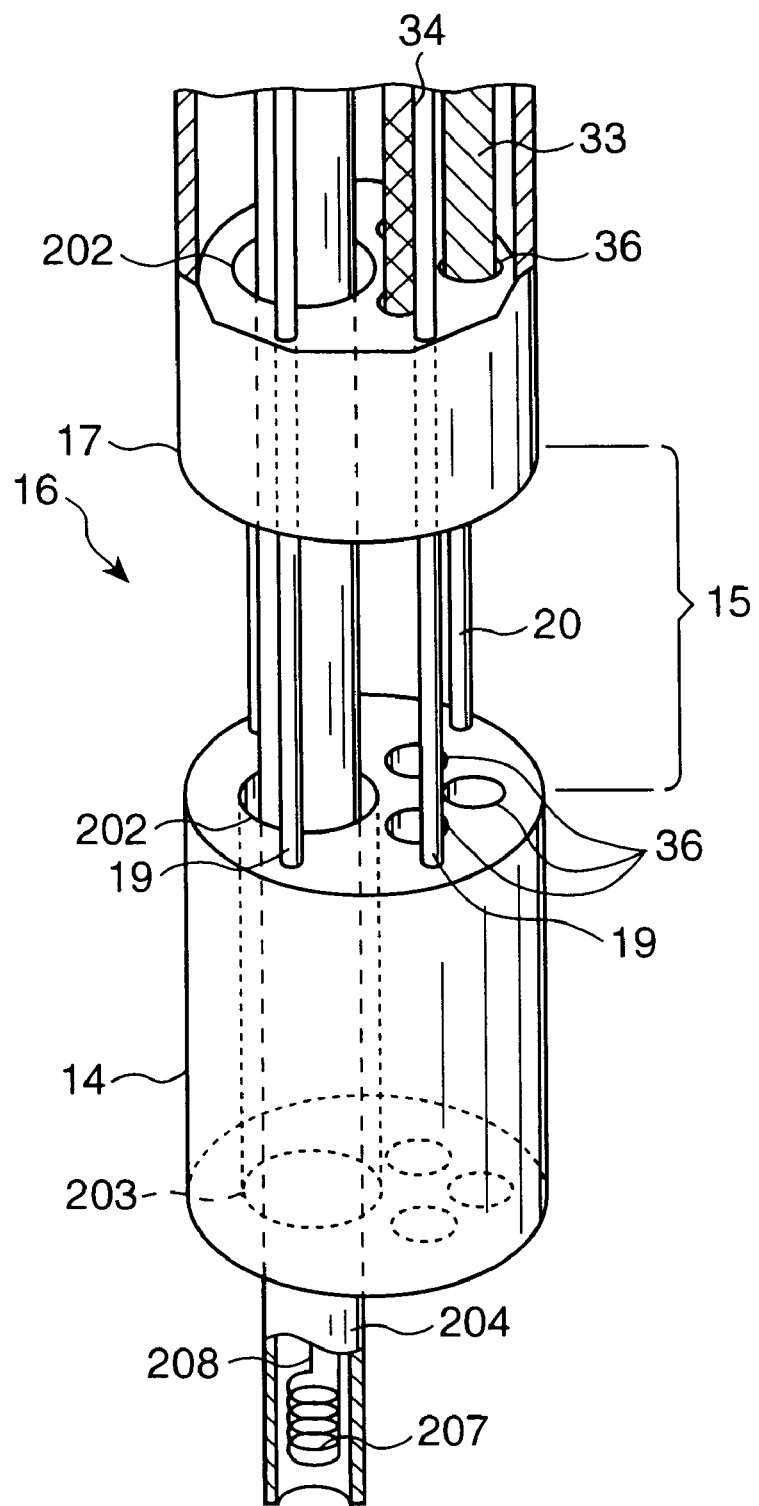
FIG. 34 shows a structure of a tip portion and a curving portion shown in FIG. 33.

FIGS. 33 and 34 relate to a fifth embodiment of the invention.

The fifth embodiment is directed to an industrial endoscope apparatus in which the grindstone 18 of the first embodiment for grinding a subject body is replaced by an eddy current examination probe for non-destructive inspection. The same parts and components as in the first embodiment are given the same reference symbols and descriptions therefor will be omitted.

As shown in FIG. 33, an insertion portion 11 of an industrial endoscope 2 of the fifth embodiment includes, in order from the tip, a tip portion 14, a curving portion 16 having a plurality of wire members and a predetermined gap 15, and a hard, an elongate insertion tube 17. A manipulation portion 13 is provided with a processing member manipulation portion side opening 201 for insertion of, for instance, a laser probe for repairing a blade by welding, an eddy current examination probe for detecting a fault in a blade, or a gripping tool for collecting fallen things in an engine. A processing tool insertion passage 202 extends from the processing member manipulation portion side opening 201 past the insertion tube 17 to a processing member tip portion side opening 203.

An eddy current examination probe 204 is inserted from the processing member manipulation portion side opening 201 and projected from the processing member tip portion side opening 203. The proximal end portion of the eddy current examination probe 204 is connected to an external eddy current measuring device 206 via a connector 205.

An eddy current pickup coil 207 such as a circular coil for generation of eddy current is incorporated in the tip portion of the eddy current examination probe 204. An eddy current signal line 208 that is connected to the eddy current pickup coil 207 extends to the connector 205. With this configuration, a detection signal produced by the eddy current pickup coil 207 is sent to the external eddy current measuring device 206 via the eddy current signal line 208. The eddy current examination probe 204 has a Teflon sheath as a cover.

The other structures are the same as in the first embodiment or the second embodiment. Further, like the third embodiment, it may be structured that the manipulation wire is driven by the motor to perform the curving control.

Next, the operation of the above-configured fifth embodiment will be described.

The insertion portion 11 is inserted from an access port to a desired blade as a subject body. While an endoscope image is observed on the LCD monitor 7, the curving portion 16 is curved by rotating the adjustment ring 23 and the insertion portion 11 is pushed or pulled so that the eddy current examination probe 204 is rendered approximately perpendicular to the blade. The tip of the eddy current examination probe 204 is moved across the wall surface of the blade (scanning is performed). When current is caused to flow through the eddy current pickup coil 205, eddy current occurs on the blade wall surface. As the eddy current pickup coil 205 is moved, the leakage magnetic field above the blade wall surface varies if a crack extends in a direction that traverses an eddy current flowing path. The crack can be detected by picking up a variation in leakage magnetic field by the eddy current pickup coil 205. The eddy current measuring device 206 causes the monitor 7 to display a waveform. Since the waveform on the monitor 7 reflects an abnormality such as a crack, a crack or the like can be detected.

The eddy current pickup coil 205 is not limited to a circular coil, and may be a rectangular coil, a bobbin coil, or a ring-shaped coil.

The invention is not limited to the above embodiments and various modifications can be made without departing from the spirit and scope of the invention.

What is claimed is:

1. An endoscope comprising:
   an elongate insertion portion;
   a tip portion disposed on a distal side of the insertion portion and formed to have a plurality of insertion passages;
   an elastic member bridging a distal end portion of the insertion portion and a proximal end portion of the tip portion so as to form therebetween a space portion having a given interval;
   a manipulation wire disposed at a position deviated from a central axis of the space portion, and extending to a proximal side of the insertion portion past the space portion, one end of the manipulation wire being fixed to the tip portion; and
   a curving mechanism connected to a proximal end portion of the manipulation wire, for changing a direction of the tip portion at the space portion by advancing or retreating the manipulation wire.

2. An endoscope comprising:
   an elongate insertion portion;
   a tip portion disposed on a distal side of the insertion portion;
   an elastic member bridging a distal end portion of the insertion portion and a proximal end portion of the tip portion so as to form therebetween a space portion having a given interval;
   a manipulation wire disposed at a position deviated from a central axis of the space portion, and extending to a proximal side of the insertion portion past the space portion, one end of the manipulation wire being fixed to the tip portion;
   a curving mechanism connected to a proximal end portion of the manipulation wire, for changing a direction of the tip portion at the space portion by advancing or retreating the manipulation wire; and
   observing means extending from the tip portion past the space portion to the proximal side of the insertion portion.

3. The endoscope according to claim 2, further comprising a processing member insertion passage extending from the tip portion past the space portion to the insertion portion, and disposed in the insertion portion.

4. The endoscope according to claim 3, wherein the elastic member is a plurality of wire members that are disposed at positions deviated from the central axis of the space portion.

5. The endoscope according to claim 3, wherein the manipulation wire is a plurality of manipulation wires that are disposed at positions deviated from the central axis of the space portion.

6. The endoscope according to claim 3, wherein the curving mechanism comprises moving means for moving the manipulation wire from a reference position to a distal side, and returning means for returning, to the reference position, the manipulation wire that has moved to the distal side.

7. The endoscope according to claim 3, wherein the curving mechanism comprises an actuator for controlling movement of the manipulation wire so that the manipulation wire can advance and retreat.

8. The endoscope according to claim 2, further comprising:
   a rotational force transmission member extending from the tip portion past the space portion to the proximal side of the insertion portion; and
   a rotary grinding member provided on a distal side of the rotational force transmission member,
   wherein the rotational force transmission member transmits rotational force of a motor to the rotary grinding member.

9. The endoscope according to claim 8, wherein the elastic member is a wire rod made of a super elastic alloy.

10. The endoscope according to claim 8, wherein the manipulation wire is a wire rod made of a super elastic alloy.

11. The endoscope according to claim 8, wherein the elastic member is a plurality of wire members that are disposed at positions deviated from the central axis of the space portion.

12. The endoscope according to claim 8, wherein the manipulation wire is a plurality of manipulation wires that are disposed at positions deviated from the central axis of the space portion.

13. The endoscope according to claim 8, further comprising a tip portion length adjustment member that can be connected to at least one of the proximal end portion of the tip portion and the distal end portion of the insertion portion.

14. The endoscope according to claim 13, wherein the tip portion length adjustment member comprises a plurality of blocks that can be connected to each other.

15. The endoscope according to claim 14, wherein the plurality of blocks include blocks having the same axial length.

16. The endoscope according to claim 14, wherein the plurality of blocks include blocks having different axial lengths.

17. The endoscope according to claim 16, wherein among the plurality of blocks, blocks disposed on a proximal side have a longer axial length than blocks disposed on a distal side.

18. The endoscope according to claim 8, wherein an internal component in the tip portion and the insertion portion is disposed at a position that is closer to the central axis than positions of the elastic member and the manipulation wire.

19. The endoscope according to claim 8, wherein the curving mechanism comprises moving means for moving the manipulation member from a reference position to a distal side, and returning means for returning, to the reference position, the manipulation wire that has moved to the distal side.

20. The endoscope according to claim 8, wherein the curving mechanism comprises an actuator for controlling movement of the manipulation wire so that the manipulation wire can advance and retreat.

21. The endoscope according to claim 20, further comprising:
    a sensor provided on the manipulation wire, for detecting a curving state; and
    a control section for controlling the actuator based on an output of the sensor.

22. The endoscope according to claim 2, further comprising:
    a processing member insertion passage extending from the tip portion past the space portion to the insertion portion, and disposed in the insertion portion; and
    an eddy current examination probe inserted in the processing member insertion passage.

23. The endoscope according to claim 22, wherein the elastic member is a wire rod made of a super elastic alloy.

24. The endoscope according to claim 22, wherein the manipulation wire is a wire rod made of a super elastic alloy.

25. The endoscope according to claim 22, wherein the elastic member is a plurality of wire members that are disposed at positions deviated from the central axis of the space portion.

26. The endoscope according to claim 22, wherein the manipulation wire is a plurality of manipulation wires that are disposed at positions deviated from the central axis of the space portion.

27. The endoscope according to claim 22, further comprising a tip portion length adjustment member that can be connected to at least one of the proximal end portion of the tip portion and the distal end portion of the insertion portion.

28. The endoscope according to claim 27, wherein the tip portion length adjustment member comprises a plurality of blocks that can be connected to each other.

29. The endoscope according to claim 28, wherein the plurality of blocks include blocks having the same axial length.

30. The endoscope according to claim 28, wherein the plurality of blocks include blocks having different axial lengths.

31. The endoscope according to claim 30, wherein among the plurality of blocks, blocks disposed on a proximal side have a longer axial length than blocks disposed on a distal side.

32. The endoscope according to claim 22, wherein an internal component in the tip portion and the insertion portion is disposed at a position that is closer to the central axis than positions of the elastic member and the manipulation wire.

33. The endoscope according to claim 22, wherein the curving mechanism comprises moving means for moving the manipulation member from a reference position to a distal side, and returning means for returning, to the reference position, the manipulation wire that has moved to the distal side.

34. The endoscope according to claim 22, wherein the curving mechanism comprises an actuator or controlling movement of the manipulation wire so that the manipulation wire can advance and retreat.

35. The endoscope according to claim 34, further comprising:
    a sensor provided on the manipulation wire, for detecting a curving state; and
    a control section for controlling the actuator based on an output of the sensor.

36. The endoscope according to claim 2, wherein the tip portion is so constructed that any of a plurality of optical adaptors having different hard portion lengths can be detachably mounted thereon.

37. The endoscope according to claim 36, further comprising:
    an optional adaptor;
    a light-emitting element provided on the optical adaptor; and
    an electrical contact provided between the optical adaptor and the tip portion, for supplying power to the light-emitting element.

38. The endoscope according to claim 37, therein the light-emitting element is an LED.

39. The endoscope according to claim 38, wherein the elastic member is a wire rod made of a super elastic alloy.

40. The endoscope according to claim 38, wherein the manipulation wire is a wire rod made of a super elastic alloy.

41. The endoscope according to claim 38, wherein the elastic member is a plurality of wire members that are disposed at positions deviated from the central axis of the space portion.

42. The endoscope according to claim 38, wherein the manipulation wire is a plurality of manipulation wires that are disposed at positions deviated from the central axis of the space portion.

43. The endoscope according to claim 38, further comprising a tip portion length adjustment member that can be connected to at least one of the proximal end portion of the tip portion and the distal end portion of the insertion portion.

44. The endoscope according to claim 43, wherein the tip portion length adjustment member comprises a plurality of blocks that can be connected to each other.

45. The endoscope according to claim 44, wherein the plurality of blocks include blocks having the same axial length.

46. The endoscope according to claim 44, wherein the plurality of blocks include blocks having different axial lengths.

47. The endoscope according to claim 46, wherein among the plurality of blocks, blocks disposed on a proximal side have a longer axial length than blocks disposed on a distal side.

48. The endoscope according to claim 38, wherein an internal component in the tip portion and the insertion portion is disposed at a position that is closer to the central axis than positions of the elastic member and the manipulation wire.

49. The endoscope according to claim 38, wherein the curving mechanism comprises moving means for moving the manipulation member from a reference position to a distal side, and returning means for returning, to the reference position, the manipulation wire that has moved to the distal side.

50. The endoscope according to claim 38, wherein the curving mechanism comprises an actuator for controlling movement of the manipulation wire so that the manipulation wire can advance and retreat.

51. The endoscope according to claim 50, further comprising:
a sensor provided on the manipulation wire, for detecting a curving state; and
a control section for controlling the actuator based on an output of the sensor.

52. The endoscope according to claim 2, wherein the elastic member is a wire rod made of a super elastic alloy.

53. The endoscope according to claim 2, wherein the manipulation wire is a wire rod made of a super elastic alloy.

54. The endoscope according to claim 2, wherein the elastic member is a plurality of wire members that are disposed at positions deviated from the central axis of the space portion.

55. The endoscope according to claim 2, wherein the manipulation wire is a plurality of manipulation wires that are disposed at positions deviated from the central axis of the space portion.

56. The endoscope according to claim 2, further comprising a tip portion length adjustment member that can be connected to at least one of the proximal end portion of the tip portion and the distal end portion of the insertion portion.

57. The endoscope according to claim 56, wherein the tip portion length adjustment member comprises a plurality of blocks that can be connected to each other.

58. The endoscope according to claim 57, wherein the plurality of blocks include blocks having the same axial length.

59. The endoscope according to claim 57, wherein the plurality of blocks include blocks having different axial lengths.

60. The endoscope according to claim 59, wherein among the plurality of blocks, blocks disposed on a proximal side have a longer axial length than blocks disposed on a distal side.

61. The endoscope according to claim 2, wherein an internal component in the tip portion and the insertion portion is disposed at a position that is closer to the central axis than positions of the elastic member and the manipulation wire.

62. The endoscope according to claim 2, wherein the curving mechanism comprises moving means for moving the manipulation wire from a reference position to a distal side, and returning means for returning, to the reference position, the manipulation wire that has moved to the distal side.

63. The endoscope according to claim 2, wherein the curving mechanism comprises an actuator for controlling movement of the manipulation wire so that the manipulation wire can advance and retreat.

64. The endoscope according to claim 18, further comprising:
a sensor provided on the manipulation wire, for detecting a curving state; and
a control section for controlling the actuator based on an output of the sensor.

65. An endoscope comprising:
an elongate insertion portion;
a tip portion disposed on a distal side of the insertion portion;
an elastic member bridging a distal end portion of the insertion portion and a proximal end portion of the tip portion so as to form therebetween a space portion having a given interval;
a manipulation wire disposed at a position deviated from a central axis of the space portion, and extending to a proximal side of the insertion portion past the space portion, one end of the manipulation wire being fixed to the tip portion;
a curving mechanism connected to a proximal end portion of the manipulation wire, for changing a direction of the tip portion at the space portion by advancing or retreating the manipulation wire; and
a processing member insertion passage extending from the tip portion past the space portion to the insertion portion, and disposed in the insertion portion,
wherein the elastic member is a wire rod made of a super elastic alloy.

66. An endoscope comprising:
an elongate insertion portion;
a tip portion disposed on a distal side of the insertion portion;
an elastic member bridging a distal end portion of the insertion portion and a proximal end portion of the tip portion so as to form therebetween a space portion having a given interval:
a manipulation wire disposed at a position deviated from a central axis of the space portion, and extending to a proximal side of the insertion portion past the space portion, one end of the manipulation wire being fixed to the tip portion;
a curving mechanism connected to a proximal end portion of the manipulation wire, for changing a direction of the tip portion at the space portion by advancing or retreating the manipulation wire; and
a processing member insertion passage extending from the tip portion past the space portion to the insertion portion, and disposed in the insertion portion,
wherein the manipulation wire is a wire rod made of a super elastic alloy.

67. An endoscope comprising:
an elongate insertion portion;

a tip portion disposed on a distal side of the insertion portion;

an elastic member bridging a distal end portion of the insertion portion and a proximal end portion of the tip portion so as to form therebetween a space portion having a given interval;

a manipulation wire disposed at a position deviated from a central axis of the space portion, and extending to a proximal side of the insertion portion past the space portion, one end of the manipulation wire being fixed to the tip portion;

a curving mechanism connected to a proximal end portion of the manipulation wire, for changing a direction of the tip portion at the space portion by advancing or retreating the manipulation wire;

a processing member insertion passage extending from the tip portion past the space portion to the insertion portion, and disposed in the insertion portion; and a tip portion length adjustment member that can be connected to at least one of the proximal end portion of the tip portion end the distal end portion of the insertion portion.

68. The endoscope according to claim 67, wherein the tip portion length adjustment member comprises a plurality of blocks that can be connected to each other.

69. The endoscope according to claim 68, wherein the plurality of blocks include blocks having the same axial length.

70. The endoscope according to claim 68, wherein the plurality of blocks include blocks having different axial lengths.

71. The endoscope according to claim 70, wherein among the plurality of blocks, blocks disposed on a proximal side have a longer axial length than blocks disposed on a distal side.

72. An endoscope comprising:

an elongate insertion portion;

a tip portion disposed on a distal side of the insertion portion;

an elastic member bridging a distal end portion of the insertion portion and a proximal end portion of the tip portion so as to form therebetween a space portion having a given interval;

a manipulation wire disposed at a position deviated from a central axis of the space portion, and extending to a proximal side of the insertion portion past the space portion, one end of the manipulation wire being fixed to the tip portion;

a curving mechanism connected to a proximal end portion of the manipulation wire, for changing a direction of the tip portion at the space portion by advancing or retreating the manipulation wire; and a processing member insertion passage extending from the tip portion past the space portion to the insertion portion, and disposed in the insertion portion, wherein an internal component in the tip portion and the insertion portion is disposed at a position that is closer to the central axis than positions of the elastic member and the manipulation wire.

73. An endoscope comprising:

an elongate insertion portion;

a tip portion disposed on a distal side of the insertion portion;

an elastic member bridging a distal end portion of the insertion portion and a proximal end portion of the tip portion so as to form therebetween a space portion having a given interval;

a manipulation wire disposed at a position deviated from a central axis of the space portion, and extending to a proximal side of the insertion portion past the space portion, one end of the manipulation wire being fixed to the tip portion;

a curving mechanism connected to a proximal end portion of the manipulation wire, for changing a direction of the tip portion at the space portion by advancing or retreating the manipulation wire;

a processing member insertion passage extending from the tip portion past the space portion to the insertion portion, and disposed in the insertion portion;

a sensor provided on the manipulation wire, for detecting a curving state; and a control section for controlling the actuator based on an output of the sensor wherein the curving mechanism comprises an actuator for controlling movement of the manipulation wire so that the manipulation wire can advance and retreat.

74. An endoscope apparatus comprising:

a tip hard portion having an observation optical system and an illumination optical system;

a cylindrical, elastically deformable curving portion provided on a proximal side of the tip hard portion;

an elongate insertion portion provided adjacent to the curving portion on a proximal side thereof;

at least three wire members having distal end portions fixed to the hard portion and proximal end portions inserted at least to the curving portion;

curving means provided on a proximal side of the insertion portion, for curving the curving portion; and one or a plurality of tip length varying blocks provided between the tip hard portion and the insertion portion, each of the one or plurality of tip length varying blocks having a fitting hole in which the at least three wire members are fitted and a fitting portion for allowing adjacent ones of the tip length varying blocks to fit into each other, wherein when at least one of the at least three wire members is advanced or retreated in a longitudinal direction of the insertion portion by the curving means, remaining one or ones of the at least three wire members that are not advanced or retreated by the curving means resist movement of the at least one wire member that is advancing or retreating, whereby all of the at least three wire members are curved to the same direction as the at least one advancing or retreating wire member is curved.

75. An endoscope comprising:

an elongate insertion portion;

a tip portion disposed on a distal side of the insertion portion;

an elastic member bridging a distal end portion of the insertion portion and a proximal end portion of the tip portion so as to form therebetween a space portion having a given interval;

a manipulation wire disposed at a position deviated from a central axis of the space portion, and extending to a proximal side of the insertion portion past the space portion, one end of the manipulation wire being fixed to the tip portion;

a curving mechanism connected to a proximal end portion of the manipulation wire, for changing a direction of the tip portion at the space portion by advancing or retreating the manipulation wire; and a tip portion length adjustment member that can be connected to at least one of the proximal end portion of the tip portion end the distal end portion of the insertion portion.

76. The endoscope according to claim 75, wherein the tip portion length adjustment member comprises a plurality of blocks that can be connected to each other.

77. The endoscope according to claim 76, wherein the plurality of blocks include blocks having the same axial length.

78. The endoscope according to claim 76, wherein the plurality of blocks include blocks having different axial lengths.

79. The endoscope according to claim 78, wherein among the plurality of blocks, blocks disposed on a proximal side have a longer axial length than blocks disposed on a distal side.

80. The endoscope according to claim 75, wherein an internal component in the tip portion and the insertion portion is disposed at a position that is closer to the central axis than positions of the elastic member and the manipulation wire.

81. The endoscope according to claim 75, wherein the curving mechanism comprises moving means for moving the manipulation wire from a reference position to a distal side, and returning means for returning, to the reference position, the manipulation wire that has moved to the distal side.

82. The endoscope according to claim 75, wherein the curving mechanism comprises an actuator for controlling movement of the manipulation wire so that the manipulation wire can advance and retreat.

83. The endoscope according to claim 75, wherein the elastic member is a wire rod made of a super elastic alloy.

84. The endoscope according to claim 75, wherein the manipulation wire is a wire rod made of a super elastic alloy.

85. The endoscope according to claim 75, wherein the elastic member is a plurality of wire members that are disposed at positions deviated from the central axis of the space portion.

86. The endoscope according to claim 75, wherein the manipulation wire is a plurality of manipulation wires that are disposed at positions deviated from the central axis of the space portion.

* * * * *